US007855225B2

(12) United States Patent
Niimi et al.

(10) Patent No.: US 7,855,225 B2
(45) Date of Patent: Dec. 21, 2010

(54) 17βHSD TYPE 5 INHIBITOR

(75) Inventors: Tatsuya Niimi, Tokyo (JP); Akio Kamikawa, Tokyo (JP); Yasushi Amano, Tokyo (JP); Tomohiko Yamaguchi, Tokyo (JP); Kenichi Suzumura, Tokyo (JP); Kentaro Enjo, Tokyo (JP); Takashi Furutani, Tokyo (JP); Akio Kakefuda, Tokyo (JP); Yutaka Kondoh, Tokyo (JP); Masaaki Hirano, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/281,416

(22) PCT Filed: Mar. 1, 2007

(86) PCT No.: PCT/JP2007/053976

§ 371 (c)(1),
(2), (4) Date: Dec. 19, 2008

(87) PCT Pub. No.: WO2007/100066

PCT Pub. Date: Sep. 7, 2007

(65) Prior Publication Data

US 2009/0181960 A1  Jul. 16, 2009

(30) Foreign Application Priority Data

Mar. 2, 2006  (JP) .............................. 2006-056827

(51) Int. Cl.
C07D 209/42 (2006.01)
A61K 31/404 (2006.01)
(52) U.S. Cl. ...................................... 514/419; 548/492
(58) Field of Classification Search ................. 514/419; 548/492
See application file for complete search history.

(56) References Cited

U.S. PATENT DOCUMENTS

| 5,283,251 | A | 2/1994 | Okada et al. |
| 5,464,863 | A | 11/1995 | Nagamine et al. |
| 5,728,712 | A * | 3/1998 | Montana et al. ............. 514/309 |
| 6,207,693 | B1 | 3/2001 | Setoi et al. |
| 6,255,306 | B1 | 7/2001 | Macor |
| 6,288,103 | B1 * | 9/2001 | Faull et al. .................. 514/419 |
| 6,333,323 | B1 | 12/2001 | Fujishita et al. |
| 6,469,046 | B1 | 10/2002 | Daines et al. |
| 6,737,435 | B1 | 5/2004 | Kettle et al. |
| 2003/0069297 | A1 | 4/2003 | Cui et al. |
| 2004/0167160 | A1 | 8/2004 | Gardinier et al. |
| 2005/0154023 | A1 | 7/2005 | Spinks et al. |
| 2006/0035884 | A1 * | 2/2006 | Neitzel et al. .......... 514/212.01 |
| 2006/0074076 | A1 | 4/2006 | Termin et al. |
| 2009/0155903 | A1 * | 6/2009 | Slade et al. ................. 435/375 |

FOREIGN PATENT DOCUMENTS

| EP | 0 902 022 A1 | 3/1999 |
| JP | 5-506010 | 9/1993 |
| JP | 6-340647 | 12/1994 |
| JP | 6-511238 | 12/1994 |
| JP | 9-104675 | 4/1997 |
| JP | 9-508137 | 8/1997 |
| JP | 2000-136182 | 5/2000 |
| JP | 2000-509719 | 8/2000 |
| JP | 2001-505193 | 4/2001 |
| JP | 2001-512716 | 8/2001 |
| JP | 2002-506077 | 2/2002 |
| JP | 2002-511852 | 4/2002 |
| JP | 2002-536359 | 10/2002 |
| JP | 2003-502367 | 1/2003 |
| JP | 2004-518669 | 6/2004 |
| JP | 2004-529855 | 9/2004 |
| JP | 2004-532194 | 10/2004 |
| JP | 2005-526033 | 9/2005 |
| WO | WO 93/03012 | 2/1993 |
| WO | WO 96/03400 | 2/1996 |
| WO | WO 96/36611 | 11/1996 |
| WO | WO 97/48697 | 12/1997 |
| WO | WO 98/24771 | 6/1998 |
| WO | WO 98/50356 | 11/1998 |
| WO | WO 99/46279 | 9/1999 |

(Continued)

OTHER PUBLICATIONS

Mouaddib et al. Synthesis, 2000, 4, 549-556.*

(Continued)

*Primary Examiner*—Rebecca L Anderson
*Assistant Examiner*—Matthew P Coughlin
(74) *Attorney, Agent, or Firm*—Finnegan, Henderson, Farabow, Garrett & Dunner, L.L.P.

(57) ABSTRACT

To provide a novel and excellent method for treating and/or preventing prostatic cancer, benign prostatic hyperplasia, acne, seborrhea, hirsutism, baldness, alopecia, precocious puberty, adrenal hypertrophy, polycystic ovary syndrome, breast cancer, lung cancer, endometriosis, leiomyoma and the like based on selective inhibitory activity against 17βHSD type 5.

It was found that an N-sulfonylindole derivative, where the indole ring is substituted by a carboxy group, a carboxy-substituted lower alkyl group or a carboxy-substituted lower alkenyl group at its carbon atom, has potent selective inhibitory activity against 17βHSD type 5 and may become a therapeutic agent and/or preventive agent for benign prostatic hyperplasia, prostatic cancer and the like without accompanying adverse drug reactions due to a decrease in testosterone, and the present invention has thus been completed.

1 Claim, No Drawings

FOREIGN PATENT DOCUMENTS

| WO | WO 99/50245 | 10/1999 |
|---|---|---|
| WO | WO 02/30895 A1 | 4/2002 |
| WO | WO 02/055517 A1 | 7/2002 |
| WO | WO 02/071827 A2 | 9/2002 |
| WO | WO 03/068220 A1 | 8/2003 |
| WO | WO 2004/064735 A2 | 8/2004 |
| WO | WO 2004/110459 A1 | 12/2004 |
| WO | WO 2005/009958 A1 | 2/2005 |
| WO | WO 2005/040112 A1 | 5/2005 |
| WO | WO 2005/113542 A2 | 12/2005 |
| WO | WO 2006/010008 A1 | 1/2006 |
| WO | WO 2007/030559 A2 | 3/2007 |
| WO | WO 2007/030574 A2 | 3/2007 |

OTHER PUBLICATIONS

Luo et al. (Cell, 2009, 136, pp. 823-837).*

Sundberg et al. J. Org. Chem. 1973, 33, 3324-3330.*

Kettle, et al., "*N*-Benzylindole-2-carboxylic acids: potent functional antagonists of the CCR2b chemokine receptor", Bioorganic & Medicinal Chemistry Letters 14, pp. 405-408, (2004).

Hopkins, et al., "Design, synthesis, and biological activity of potent and selective inhibitors of mast cell tryptase", Bioorganic & Medicinal Chemistry Letters 15, pp. 2734-2737, (2005).

Mahboobi, et al., "Bis(1*H*-2-indolyl) methanones as a Novel Class of Inhibitors of the Platelet-Derived Growth Factor Receptor Kinase", J. Med. Chem. 45, pp. 1002-1018, (2002).

Mcconnell, et al., "The Long-Term Effect of Doxazosin, Finasteride, and Combination Therapy on the Clinical Progression of Benign Prostatic Hyperplasia", The New Englad Journal of Medicine, vol. 349, No. 25, pp. 2387-2398, (Dec. 18, 2003).

Labrie, et al., "DHEA and Its Transformation into Androgens and Estrogens in Peripheral Target Tissues: Intracrinology", Frontiers in Neuroendocrinolgy 22, pp. 185-212, (2001).

Span, et al., "Selectivity of Finasteride as an in Vivo Inhibitor of 5α-Reductase Isozyme Enzymatic Activity in the Human Prostate", The Journal of Urology, vol. 61, pp. 332-337, (Jan. 1999).

Crawford, et al., "Therapeutic Controversies: Endocrine Therapy of Prostate Cancer: Optimal form and Appropriate Timing", Journal of Clinical Endocrinology and Metabolism, vol. 80, No. 4, pp. 1062-1078, (1995).

Mohler, et al., "The Adrogen Axis in Recurrent Prostate Cancer", Clinical Cancer Research, vol. 10, pp. 440-448, (Jan. 15, 2004).

Lin, et al., "Characterization of a monoclonal antibody for human aldo-keto reductase AKR1C3 (type 2 3-α-hydoxysteroid dehydrogenase/type 5 17β-hydroxysteroid dehydrogenase); immunohistochemical detection in breast and prostate", Steroids 69, pp. 795-801, (2004).

Geissler, et al., "Male pseudohermaphroditism caused by mutations of testicular 17β-hydroxysteroid dehydrogenase 3", Nature Genetics, vol. 7, pp. 34-39, (May 1994).

Labrie, et al., "Endocrine and Intracine Sources of Androgens in Women: Inhibition of Breast Cancer and Other Roles of Androgens and Their Percursor Dehydroepiandrosterone", Endocrine Reviews 24(2), pp. 152-182, (2003).

Palackal, et al., "Activation of Polycyclic Aromatic Hydrocarbon *trans*-Dihydrodiol Proximate Carcinogens by Human Aldo-keto Reductase (AKR1C) Enzymes and Their Functional Overexpression in Human Lung Carcinoma (A549) Cells", The Journal of Biological Chemistry, vol. 277, No. 27, pp. 24799-24808, (2002).

Lan, et al., "Oxidative damage-related genese *AKR1C3* and *OGG1* modulate risks for lung cancer due to exposure to PAH-rich coal combustion emissions", Carcinogenesis, vol. 25, No. 11, pp. 2177-2181, (2004).

Lovering, et al., "Crystal Structures of Prostaglandin $D_2$ 11-Ketereductase (AKR1C3) in Complex with the Nonsteroidal Anti-Inflammatory Drugs Flufenamic Acid and Indomethacin", Cancer Research 64, pp. 1802-1801, (Mar. 1, 2004).

Mouaddib, et al., "Synthesis of Indolo[3,2-*c*]quinoline and Pyrido[3',2':4,5][3,2-*c*]quinoline Derivatives", Synthesis, No. 4, pp. 549-556, (2000).

Clark, et al., "OptDesign: Extending Optimizable *k*-Dissimilarity Selection to Combinatorial Library Design", J. Chem. Inf. Comput. Sci, No. 43, pp. 829-836, (2003).

Stanbrough, et al., "Increased Expression of Genes Convering Adrenal Androgens to Testosterone in Androgen-Independent Prostate Cancer", Cancer Res., No. 66, (5), pp. 2815-2825, (Mar. 1, 2006).

Brožič, et al., "Cinnamic acids as new inhibitors of 17β-hydroxysteroid dehydrogenase type 5 (AKR1C3)", Molecular and Cellular Endocrinology 248, pp. 233-235, (2006).

Passarella, et al., "Cyclodimerization of indol-2-ylacetylenes. An example of intermolecular enyne-alkyne cycloaddition", J. Chem. Soc. Perkin Trans. 1, pp. 127-129, (2001).

Rare Chemicals Catalogue, 1H-Indole-3-Carboxylic Acid, 1-[(4-Methylphenyl)Sulfonyl] Order No. AL BE 0453, SciFinder, p. 1 of 1, (Oct. 6, 2008).

Muratake, et al., "Preparation of Alkyl-Substituted Indoles in the Benzene Portion, Part 2", Heterocycles, vol. 29, No. 4, pp. 783-794, (1989).

Nicolaou, et al., "Synthesis of N-Protected 1*H*-Indole-5-Carboxylic Acids With Aldose Reductase Inhibitory Potential", Oppi Briefs, vol. 34, No. 5, pp. 511-514, (2002).

Andreani, et al., "Indole Derivatives Related to Lonidamine", Arch. Pharm., No. 317, pp. 847-814, (1984).

Miki, et al., "Reaction of Indole-2,3-Dicarboxylic Anhydride With Grignard Reagents: Synthesis of 2-Acylindoles", Heterocycles, vol. 45, No. 6, pp. 1143-1150, (1997).

Conway, et al., "Approaches to the Generation of 2,3-Indolyne", Heterocycles, vol. 34, No. 11, pp. 2095-2108, (1992).

European Search Report dated Oct. 12, 2009.

Chinese Office Action dated Jul. 13, 2010, in Chinese Patent Application No. 2007/80007213.5 (9 pages) with English translation (4 pages).

* cited by examiner

17βHSD TYPE 5 INHIBITOR

TECHNICAL FIELD

The present invention relates to an indole compound having a pharmacological activity and a pharmaceutically acceptable salt thereof. The present invention also relates to a medicament or a pharmaceutical composition containing the indole compound or a pharmaceutically acceptable salt thereof described above as an active ingredient.

BACKGROUND ART

Benign prostatic hyperplasia (BPH) is a disease mainly occurring in elder males aged 50 years or above and accompanying urinary disturbance, and its incidence rate increases as an increase in age. The number of patients with BPH in Japan has been constantly increasing in recent years with rapid aging of population structure (Non-patent Document 1). BPH remarkably deteriorates the quality of life of the aged males due to urinary disturbance, and it is an important disease in terms of medical economics since it is most frequently diagnosed and treated in medical practice in the department of urology.

It has been found that two factors, that is, direct urethral compression due to hypertrophy of the prostate (mechanical obstruction) and elevation of intraurethral pressure due to overcontraction of the prostatic smooth muscle via the sympathetic nerve (functional obstruction), are simultaneously involved in urinary disturbance accompanying BPH. Drug therapy can deal with the both of the mechanisms, and 5α-reductase inhibitors are mainly used for the mechanical obstruction and α-1-sympatholytic agents (α1 blockers) for the functional obstruction. 5α reductase inhibitors regress the prostate due to their anti-androgenic effect based on the suppression of conversion from testosterone to more potent 5α-dehydrotestosterone (DHT) of androgen by a 5α-reductase. Only the prostatic epithelium regresses, however, and it takes a long period of time (several weeks to several months) for its drug efficacy to appear. Since α1-blockers exert their drug efficacy swiftly after administration and are excellent in safety, on the other hand, α1-blockers are now the first-line agent for the treatment of BPH. Since long-term clinical studies of a 5α-reductase inhibitor have revealed, however, that the inhibitor preferentially delays the transfer to invasive therapy as compared with an α1-blocker used alone, and the like (Non-patent Document 2), the usefulness of 5α-reductase inhibitors has recently been recognized again.

It has been considered that DHT in the prostate is produced by 5α-reductase from testosterone, which is produced in the testes and secreted endocrinologically to the prostate. It has been reported recently, however, that about half of DHT and its precursor, testosterone in prostate are synthesized from dehydroepiandrosterone (DHEA), an adrenal steroid, in cells of the prostate (Non-patent Document 3). Such sex hormone production system in cells of the sex hormone target organs is called intracrinology.

It is difficult for 5α-reductase inhibitors to inhibit the local testosterone synthesis (intracrine testosterone synthesis) in the prostate. For example, it has been reported that the concentration of DHT in the prostate of the patients with BPH decreased after the administration of finasteride, a 5α-reductase inhibitor, to about 20% of the concentration before the administration, while the concentration of testosterone, a precursor, in the prostate increased 4-fold inversely (Non-patent Document 4). It means that although the 5α-reductase inhibitor has an effect of reducing DHT concentration in prostate, it has no effect of reducing the concentration of testosterone in prostate and elevates the concentration instead. Since testosterone has an androgen receptor binding activity in the order of half that of DHT, this local elevation of the concentrations of testosterone in prostate is considered to be partly attributable to insufficient drug efficacy of finasteride for BPH.

Anti-androgen therapies using surgical castration and gonadotropin releasing hormone agonists are also used for the treatment of prostatic cancer. These anti-androgen therapies have been reported to exert an insufficient effect of reducing the concentrations of testosterone in prostate. For example, in patients with prostatic cancer who receive the anti-androgen therapy, the concentration of testosterone in blood decreased to about 10% of the concentration before the therapy, while the concentration of dehydrotestosterone in prostate remained at about 50% (Non-patent Document 5). It suggests that the concentration of testosterone in prostate is neither reduced sufficiently. Further, androgen receptors were localized in nuclei also in a prostatic cancer recurring after anti-androgen therapy (hormone refractory prostate cancer), and no significant difference was observed between the concentration of testosterone in recurrent prostatic cancer tissue and that in the normal prostate (Non-patent Document 6). These reports strongly suggest that the effect of reducing the concentrations of testosterone in prostate in existing therapeutic methods is quite insufficient for the treatment of recurrent prostatic cancer and that suppression of the testosterone synthesizing mechanism in prostate, that is, intracrine testosterone synthesis in prostate may be a new target of the prostatic cancer therapy.

Based on the known arts described above, since inhibitors of intracrine testosterone synthesis in prostate have an effect of reducing the concentrations of testosterone in prostate and no effect of reducing the concentrations of testosterone in blood, the inhibitors are expected to be very attractive agents for the treatment of BPH, which can reduce not only the concentrations of testosterone but also the concentrations of DHT in prostate (1) and can avoid the adverse drug reactions due to the suppression of the concentrations of the testosterone in blood derived from testes (2).

17β-hydroxysteroid dehydrogenase (17βHSD) is essential for the biosynthesis of testosterone. There are several subtypes of 17β-hydroxysteroid dehydrogenase. 17β-hydroxysteroid dehydrogenase type 5 (17βHSD type 5) is highly expressed in a human prostate and the increases of the expression were reported for prostatic cancer and recurrent prostatic cancer (Patent Document 1, and Non-patent Documents 7, 18). On the other hand, almost all the testosterone in blood is biosynthesized by 17β-hydroxysteroid dehydrogenase type 3 (17βHSD type 3) in testes and the expression of 17βHSD type 3 is scarcely observed in other tissues including the prostate (Non-patent Document 8). 17βHSD type 5 is thus considered to be attributable to the intracrine testosterone synthesis in prostate and selective inhibitors for 17βHSD type 5 are expected to suppress intracrine testosterone synthesis in prostate selectively. Further, since attribution of 17βHSD type 5 has been pointed out also in estrogen-dependent tissues such as the breast and the like, the selective inhibitors are expected to be effective for estrogen-dependent diseases such as breast cancer and the like (Patent Document 1 and Non-patent Document 9). In addition, since AKR1C3 (another name for 17βHSD type 5), which is a subtype of aldo-keto reductase (AKR), metabolizes polycyclic aromatic hydrocarbon (PAH) to generate reactive oxygen species (ROS) (Non-patent Document 10) and since single nucleotide polymorphism (SNP) of AKR1C3 gene relating to oxidation stress correlates to a risk of lung cancer (Non-patent Document 11), it is suggested that the activity of AKR1C3 in the lungs increases a risk of lung cancer via biosynthesis of ROS from PAH. Selective inhibitors of 17βHSD type 5 are expected to be effective for lung cancer.

As 17βHSD type 5 inhibitors, steroid derivatives (Patent Document 1) and nonsteroidal anti-inflammatory drugs (NSAIDs) such as flufenamic acid, indomethacin and the like (Non-patent Document 12), cinnamic acid derivatives (Non-patent Document 20) and the like have been reported. Although the mechanism of action is different, a certain type of indazole derivative is known to be effective for BPH (Patent Document 7). However, it has not been known that indole derivatives such as the compound of the present invention inhibit 17βHSD type 5 and are effective for BPH.

At the same time, although a certain type of indole compound is known to be effective for Ehrlich ascites cancer (Non-patent Document 19), they are not known to be effective for another type of cancer, prostatic cancer and BPH. In addition, although the known compounds described below having structures similar to the structure of the compound of the present invention are excluded from the compound of the present invention, the compounds described below are not known to be used for the treatment or prevention of the diseases described for the present invention.

[formula 1]

known compound 1

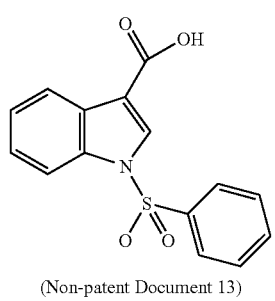

(Non-patent Document 13)

known compound 2

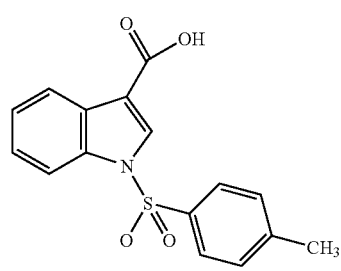

(Non-patent Document 14)

known compound 3

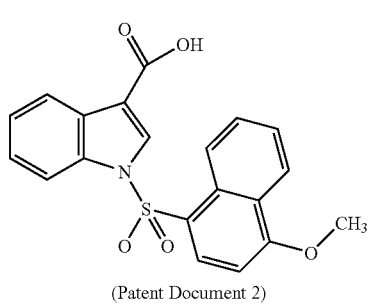

(Patent Document 2)

-continued known compound 4

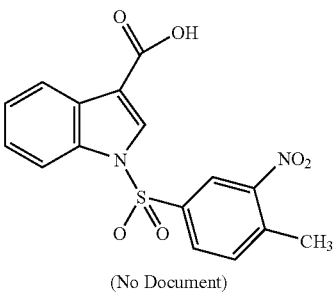

(No Document)

known compound 5

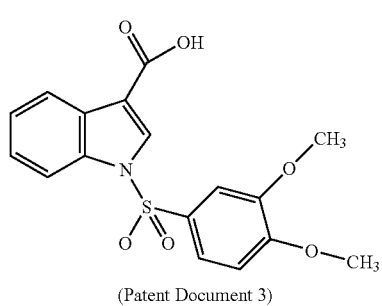

(Patent Document 3)

known compound 6

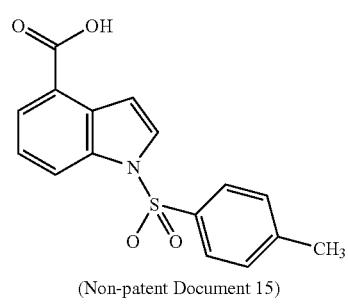

(Non-patent Document 15)

known compound 7

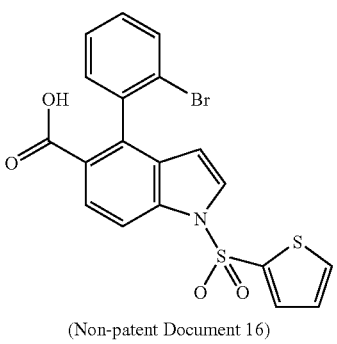

(Non-patent Document 16)

known compound 8

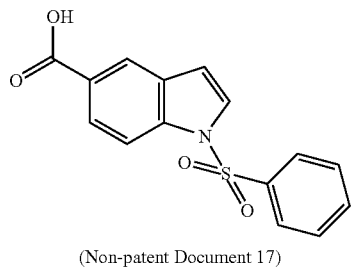

(Non-patent Document 17)

-continued known compound 9

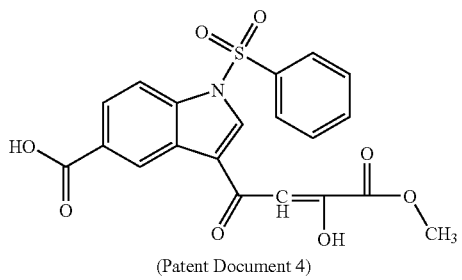

(Patent Document 4)

known compound 10

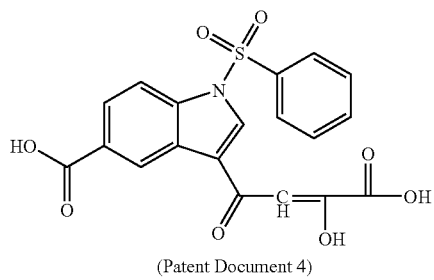

(Patent Document 4)

known compound 11

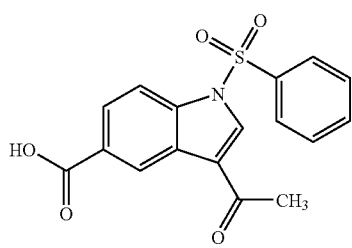

(Patent Document 4)

known compound 12

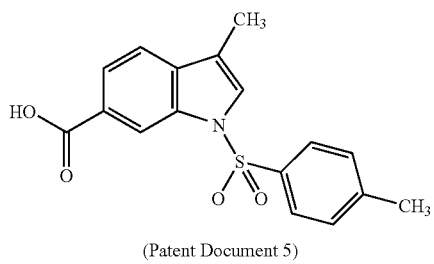

(Patent Document 5)

known compound 13

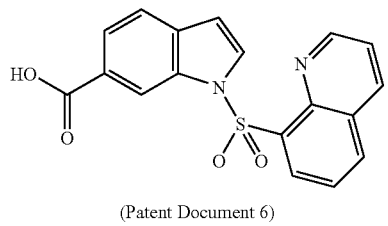

(Patent Document 6)

Patent Document 1: International Publication WO99/46279

Patent Document 2: International Publication WO03/68220

Patent Document 3: International Publication WO96/36611

Patent Document 4: International Publication WO99/50245

Patent Document 5: International Publication WO97/48697

Patent Document 6: Japanese Patent Laid-open No. H09-104675

Patent Document 7: International Publication WO2004/064735

Non-patent Document 1: National Institute of Population and Social Security Research: Population Prediction for Japan (estimated in January, 1997), Japan, 1997, p. 1900

Non-patent Document 2: The New England Journal of Medicine, 2003, Vol. 349, p. 2387-2398

Non-patent Document 3: Frontier in Neuroendocrinology, 2003, vol. 22, p.

Non-patent Document 4: Journal of Urology, 1999, Vol. 161, p. 332-337

Non-patent Document 5: The Journal of Clinical Endocrinology and Metabolism, 1995, Vol. 80, p. 1066-1071

Non-patent Document 6: Clinical Cancer Research, 2004, Vol. 10, p. 440-448

Non-patent Document 7: Steroids, 2004, Vol. 69, p. 795-801

Non-patent Document 8: Nature Genetics, 1994, Vol. 7, p. 34-39

Non-patent Document 9: Endocrine Reviews, 2003, Vol. 24, p. 152-182

Non-patent Document 10: The Journal of Biological Chemistry, 2002, Vol. 277, No. 27, p. 24799-24808

Non-patent Document 11: Carcinogenesis, 2004, Vol. 25, No. 11, p. 2177-2181

Non-patent Document 12: Cancer Research, 2004, Vol. 64, p. 1802-1810

Non-patent Document 13: Synthesis, 2000, No. 4, p. 549-556

Non-patent Document 14: Rare Chemicals Catalogue, Rare Chemicals Gmbh Order No. AL BE 0453

Non-patent Document 15: Heterocycles, 1989, Vol. 29, No. 4, p. 783-794

Non-patent Document 16: Journal of Chemical Information and Computer Sciences, 2003, Vol. 43, No. 3, p. 829-836

Non-patent Document 17: Organic Preparations and Procedures International, 2002, Vol. 34, No. 5, p. 511-514

Non-patent Document 18: Cancer Research, 2006, Vol. 66, p. 2815-2825

Non-patent Document 19: Archiv der Pharmazie—Pharmaceutical and Medicinal Chemistry, 1984, Vol. 317, p. 847-851

Non-patent Document 20: Molecular and Cellular Endocrinology, 2006, Vol. 248, p. 233-235

DISCLOSURE OF THE INVENTION

Problems to be Solved by the Invention

An object of the present invention is to provide a compound useful as a medicament having selective inhibitory activity against 17βHSD type 5, in particular as a therapeutic agent for benign prostatic hyperplasia and prostate cancer.

Measures for Solving the Problems

The present inventors have keenly studied about compounds having selective inhibitory activity against 17βHSD type 5, as a result, found that N-sulfonylindole derivatives, where the indole ring is substituted by a carboxy group, a carboxy-substituted lower alkyl group or a carboxy-substituted lower alkenyl group at its carbon atom, have a potent selective inhibitory activity against 17βHSD type 5 and can be a therapeutic agent and/or a preventive agent for diseases in which 17βHSD type is involved such as benign prostatic hyperplasia and prostatic cancer without accompanying adverse drug reactions due to a decrease in testosterone, and completed the present invention.

The present invention relates to a compound represented by general formula (I) or a pharmaceutically acceptable salt thereof.

[formula 2]

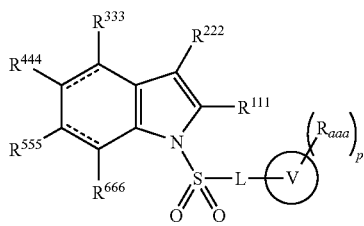

(I)

In formula (I), L represents lower alkylene, lower alkenylene, —O-lower alkylene, lower alkylene-O— or a bond, in which each of the groups may be substituted by aryl(s);

[formula 3]

represents an aryl, cycloalkyl or heterocyclic group;

Raaa, which is the same or different, represents hydrogen, lower alkyl, halogen, cyano, lower alkenyl, halogen-substituted lower alkyl, lower alkyl-O—, cyano lower alkyl-O—, halogen-substituted lower alkyl-O—, aryl, heteroaryl, aryl-O—, heteroaryl-O—, aryl lower alkyl, acyl-O—, acyl, heteroaryl lower alkyl-O—, lower alkylthio, lower alkylsulfonyl, oxo, nitro, amino, mono-lower alkylamino, di-lower alkylamino, acylamino or arylamino, in which the aryl, the heteroaryl, and the aryl and the heteroaryl moieties of each of the aryl-O—, heteroaryl-O—, heteroaryl lower alkyl-O—, aryl lower alkyl and arylamino in the Raaa may be substituted by lower alkyl(s), lower alkyl-O-(s), halogen(s) or halogen-substituted lower alkyl(s);

$R^{111}$, $R^{222}$, $R^{333}$, $R^{444}$, $R^{555}$ and $R^{666}$ represent hydrogen or an appropriate substituent, in which at least one of the $R^{111}$, $R^{222}$, $R^{333}$, $R^{444}$, $R^{555}$ and $R^{666}$ represents carboxy, carboxy-substituted lower alkyl or carboxy-substituted lower alkenyl, and any adjacent two groups of $R^{333}$, $R^{444}$, $R^{555}$ and $R^{666}$ together may form a lower alkylene dioxy group;

a double line of a solid line and a dotted line represents a single bond or a double bond; and p represents an integer of 1 to 15.

Further, the present invention relates to a compound represented by general formula (III) or a pharmaceutically acceptable salt thereof.

[formula 4]

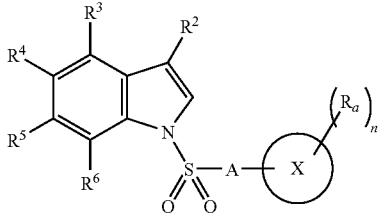

(III)

In formula (III), A represents lower alkylene, lower alkenylene, —O-lower alkylene, lower alkylene-O— or a bond, in which each of the groups may be substituted by aryl(s);

[formula 5]

represents an aryl, cycloalkyl or heterocyclic group;

Ra, which is the same or different, represents hydrogen, lower alkyl, halogen, cyano, lower alkenyl, halogen-substituted lower alkyl, lower alkyl-O—, cyano lower alkyl-O—, halogen-substituted lower alkyl-O—, aryl, heteroaryl, aryl-O—, heteroaryl-O—, aryl lower alkyl, acyl-O—, acyl, heteroaryl lower alkyl-O—, lower alkylthio, lower alkylsulfonyl, oxo, nitro, amino, mono-lower alkylamino, di-lower alkylamino, acylamino or arylamino, in which the aryl, the heteroaryl, and the aryl and the heteroaryl moieties of each of the aryl-O—, heteroaryl-O—, heteroaryl lower alkyl-O—, aryl lower alkyl and arylamino in the Ra may be substituted by lower alkyl(s), lower alkyl-O—(s), halogen(s) or halogen-substituted lower alkyl(s);

$R^2$ to $R^6$ represent hydrogen or an appropriate substituent, in which at least one of $R^2$ to $R^6$ represents carboxy, and any adjacent two groups of $R^3$ to $R^6$ together may form a lower alkylene dioxy group; and n represents an integer of 1 to 15.

Provided that when $R^2$ is carboxy, $R^3$, $R^4$, $R^5$ and $R^6$ are hydrogen,

[formula 6]

is 1-naphthyl, A is a bond and n is 1; Ra is a group other than 4-methoxy (namely, other than the known compound 3): when $R^2$ is carboxy, and $R^3$, $R^4$, $R^5$ and $R^6$ are hydrogen,

[formula 7]

is phenyl, A is a bond, and n is 1; Ra is a group other than hydrogen and 4-methyl (namely, other than the known compounds 1 and 2): and when n is 2, a combination of two Ra's is selected from combinations of groups other than a combination of 4-methyl and 3-nitro and a combination of 3-methoxy and 4-methoxy (namely, other than the known compounds 4 and 5):

when $R^3$ is carboxy, $R^2$, $R^4$, $R^5$ and $R^6$ are hydrogen,

[formula 8]

is phenyl, A is a bond, and n is 1; Ra is a group other than 4-methyl (namely, other than the known compound 6):

when $R^4$ is carboxy, $R^2$, $R^5$ and $R^6$ are hydrogen, $R^3$ is 2-bromophenyl,

[formula 9]

is 2-thienyl, A is a bond, and n is 1; the Ra is a group other than hydrogen (namely, other than the known compound 7):

when $R^4$ is carboxy, $R^2$, $R^3$, $R^5$ and $R^6$ are hydrogen,

[formula 10]

is phenyl, A is a bond, and n is 1; Ra is a group other than hydrogen (namely, other than the known compound 8):

when $R^4$ is carboxy, $R^3$, $R^5$ and $R^6$ are hydrogen, $R^2$ is 3-methoxycarbonyl-3-hydroxyacryloyl,

[formula 11]

is phenyl, A is a bond, and n is 1; Ra is a group other than hydrogen (namely, other than the known compound 9):

when $R^4$ is carboxy, $R^3$, $R^5$ and $R^6$ are hydrogen, $R^2$ is 3-carboxy-3-hydroxyacryloyl,

[formula 12]

is phenyl, A is a bond, and n is 1; Ra is a group other than hydrogen (namely, other than the known compound 10):

when $R^4$ is carboxy, $R^3$, $R^5$ and $R^6$ are hydrogen, $R^2$ is acetyl,

[formula 13]

is phenyl, A is a bond, and n is 1; Ra is a group other than hydrogen (namely, other than the known compound 11):

when $R^5$ is carboxy, $R^2$ is methyl, $R^3$, $R^4$ and $R^6$ are hydrogen,

[formula 14]

is phenyl, A is a bond, and n is 1; Ra is a group other than 4-methyl (namely, other than the known compound 12):

when $R^5$ is carboxy, $R^2$, $R^3$, $R^4$ and $R^6$ are hydrogen,

[formula 15]

is 8-quinolinyl, A is a bond, and n is 1; Ra is a group other than hydrogen (namely, other than the known compound 13).

Further, the present invention relates to a pharmaceutical composition comprising the compound represented by formula (I) and/or formula (III).

Further, the present invention relates to a therapeutic agent and/or a preventive agent for a disease associated with 17βHSD type 5 containing the compound represented by formula (I) and/or formula (III) or a pharmaceutically acceptable salt thereof as an active ingredient.

Further, the present invention relates to use of the compound represented by formula (I) and/or formula (III) or a pharmaceutically acceptable salt thereof for producing a medicament for a treatment and/or prevention of a disease associated with 17βHSD type 5.

Further, the present invention relates to a therapeutic and/or preventive method for a disease associated with 17βHSD type 5 administering an effective amount of the compound represented by formula (I) and/or formula (III) or a pharmaceutically acceptable salt thereof to a patient.

Further, the present invention relates to an inhibitor of 17βHSD type 5 containing the compound represented by formula (I) and/or formula (III) or a pharmaceutically acceptable salt thereof.

Further, the present invention relates to a commercial package containing a pharmaceutical composition containing the compound represented by formula (I) and/or formula (III) or a pharmaceutically acceptable salt thereof; and a description that the compound represented by formula (I) and/or formula (III) or a pharmaceutically acceptable salt thereof is capable of being used or should be used for a treatment and/or prevention of prostatic cancer, benign prostatic hyperplasia, acne, seborrhea, hirsutism, baldness, alopecia, precocious puberty, adrenal hypertrophy, polycystic ovary syndrome, breast cancer, endometriosis, lung cancer or leiomyoma.

Further, the present invention relates to a therapeutic agent and/or a preventive agent for a disease associated with 17βHSD type 5 containing a compound represented by general formula (II) or a pharmaceutically acceptable salt thereof as an active ingredient.

[formula 16]

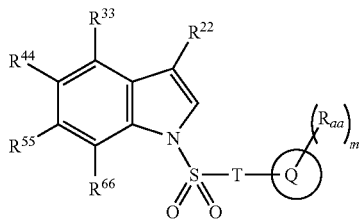

(II)

In formula (II), T represents lower alkylene, lower alkenylene, —O-lower alkylene, lower alkylene-O— or a bond, in which each of the groups may be substituted by aryl(s);

[formula 17]

represents an aryl, cycloalkyl or heterocyclic group;

Raa, which is the same or different, represents hydrogen, lower alkyl, halogen, cyano, lower alkenyl, halogen-substituted lower alkyl, lower alkyl-O—, cyano lower alkyl-O—, halogen-substituted lower alkyl-O—, aryl, heteroaryl, aryl-O—, heteroaryl-O—, aryl lower alkyl, acyl-O—, acyl, heteroaryl lower alkyl-O—, lower alkylthio, lower alkylsulfonyl, oxo, nitro, amino, mono-lower alkylamino, di-lower alkylamino, acylamino or arylamino, in which the aryl, the heteroaryl, and the aryl and the heteroaryl moieties of each of the aryl-O—, heteroaryl-O—, heteroaryl lower alkyl-O—, aryl lower alkyl and arylamino in the Raa may be substituted by lower alkyl(s), lower alkyl-O-(s), halogen(s) or halogen-substituted lower alkyl(s);

$R^{22}$, $R^{33}$, $R^{44}$, $R^{55}$ and $R^{66}$ represent hydrogen or an appropriate substituent, in which at least one of $R^{22}$, $R^{33}$, $R^{44}$, $R^{55}$ and $R^{66}$ represents carboxy, and any of adjacent two groups of $R^{33}$, $R^{44}$, $R^{55}$ and $R^{66}$ together may form a lower alkylene dioxy group; and m represents an integer of 1 to 15.

Further, the present invention relates to use of the compound represented by formula (II) or a pharmaceutically acceptable salt thereof for producing a medicament for a treatment and/or prevention of a disease associated with 17βHSD type 5.

Further, the present invention relates to a therapeutic and/or preventive method for a disease associated with 17βHSD type 5 administering an effective amount of the compound represented by formula (II) or a pharmaceutically acceptable salt thereof to a patient.

Further, the present invention relates to an inhibitor of 17βHSD type 5 containing the compound represented by formula (II) or a pharmaceutically acceptable salt thereof.

Further, the present invention relates to a commercial package containing a pharmaceutical composition containing the compound represented by formula (II) or a pharmaceutically acceptable salt thereof; and a description that the compound represented by formula (II) or a pharmaceutically acceptable salt thereof is capable of being used or should be used for a treatment and/or prevention of prostatic cancer, benign prostatic hyperplasia, acne, seborrhea, hirsutism, baldness, alopecia, precocious puberty, adrenal hypertrophy, polycystic ovary syndrome, breast cancer, endometriosis, lung cancer or leiomyoma.

EFFECT OF THE INVENTION

The compound of the present invention represented by formula (I) and/or formula (II) and/or formula (III) inhibits 17βHSD type 5 selectively. Accordingly, the compound of the present invention is useful as a preventive and/or therapeutic agent for diseases associated with 17βHSD type 5, for example, diseases associated with androgen, since androgen synthesis is suppressed by the inhibition of 17βHSD type 5. Examples of the diseases associated with androgen include prostatic cancer, benign prostatic hyperplasia, acne, seborrhea, hirsutism, baldness, alopecia, precocious puberty, adrenal hypertrophy, polycystic ovary syndrome, breast cancer, endometriosis and leiomyoma. In addition, since AKR1C3 (another name for 17βHSD type 5), which is a subtype of aldo-keto reductase (AKR), metabolizes polycyclic aromatic hydrocarbon (PAH) to generate reactive oxygen species (ROS) and since single nucleotide polymorphism (SNP) of AKR1C3 gene relating to oxidation stress correlates to a risk of lung cancer, lung cancer is also included in the diseases associated with 17βHSD type 5. The compound of the present invention is therefore useful as a therapeutic agent and/or a preventive agent for these diseases.

In addition, since 17βHSD type 5 is considered to be attributable to intracrine androgen synthesis in prostate, selective inhibitors of 17βHSD type 5 are expected to suppress intracrine androgen synthesis in prostate selectively. Accordingly, the compound of the present invention is particularly useful as a therapeutic agent and/or a preventive agent for diseases associated with androgen in prostate, that is, prostatic cancer and benign prostatic hyperplasia.

Further, since the compound of the present invention does not influence the concentrations of testosterone in blood, the compound may be a therapeutic drug and/or preventive drug for benign prostatic hyperplasia and prostatic cancer without adverse drug reactions such as sexual function disorder due to the reduction of the concentrations of testosterone in blood, and the like.

BEST MODE FOR CARRYING OUT THE INVENTION

The present invention will be described in detail below.

The compound of the present invention represented by formula (I) and/or formula (II) and/or formula (III) will be then described in detail.

Various preferred examples of the definitions included in the range of the present invention in the description above and below in the present Description will be described in detail below.

The term "lower" refers to a group containing 1 to 6 carbon atoms, unless otherwise particularly noted. "Lower alkyl" refers to a linear or branched aliphatic hydrocarbon containing 1 to 6 carbon atoms. For example, methyl, ethyl, propyl, isopropyl, butyl, isobutyl, tert-butyl, pentyl, hexyl and the like are included.

"Lower alkylene" refers to a divalent group formed by removing a hydrogen atom from "lower alkyl".

The expression "—O—" used in the definitions refers to a divalent oxygen atom. For example, the expression of lower alkyl-O— represents lower alkoxy. Lower alkoxy refers to a linear or branched aliphatic hydrocarbonoxy group containing 1 to 6 carbon atoms. For example, methoxy, ethoxy, propoxy, isopropoxy, butoxy, isobutoxy, tert-butoxy, pentoxy, hexoxy and the like are included. In addition, for the definition of L in formula (I), it means that the oxygen atom in —O-lower alkylene is a group binding to an S atom in formula (I) and that the oxygen atom in lower alkylene-O— is a group binding to

[formula 18]

$$\text{V}$$

in formula (I).

"Aryl" refers to a group formed by an aromatic hydrocarbon ring containing 6 to 14 carbon atoms, preferably 6 to 10 carbon atoms. For example, phenyl, naphthyl, anthryl and the like are included.

"Heterocyclic group" refers to a 5 to 6-membered monocyclic heteroaromatic group containing 1 to 4 heteroatoms selected from O, N and S, or a 8 to 10-membered bicyclic heteroaromatic groups containing 1 to 6 heteroatoms selected from O, N and S, or a 11 to 14-membered tricyclic heteroaromatic group containing 1 to 8 heteroatoms selected from O, N and S. Preferable examples thereof include 3 to 6-membered monocyclic heteroaromatic groups containing 1 to 4 nitrogen atoms, for example, pyrrolyl, imidazolyl, pyrazolyl, pyridyl, pyrimidinyl, pyrazinyl, pyridazinyl, triazolyl (for example, 4H-1,2,4-triazolyl, 1H-1,2,3-triazolyl, 2H-1,2,3-triazolyl and the like), tetrazolyl (for example, 1H-tetrazolyl, 2H-tetrazolyl and the like) and the like; fused cyclic heteroaromatic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (for example, tetrazolo[1,5-b]pyridazinyl and the like), quinoxalinyl, imidazopyridyl (for example, imidazo[1,2-a]pyridyl and the like) and others; 3 to 6-membered monocyclic heteroaromatic groups containing one oxygen atom, for example, pyranyl, furyl and the like; 3 to 6-membered monocyclic heteroaromatic groups containing 1 to 2 sulfur atoms, for example, thienyl and the like; 3 to 6-membered monocyclic heteroaromatic groups containing 1 to 2 oxygen atoms and 1 to 3 nitrogen atoms, for example, oxazolyl, isooxazolyl, oxadiazolyl (for example, 1,2,4-oxadiazolyl, 1,3,4-oxadiazolyl, 1,2,5-oxadiazolyl and the like) and others; fused cyclic heteroaromatic groups containing 1 to 2 oxygen atoms and 1 to 3 nitrogen atoms, for example, benzofurazanyl, benzoxazolyl, benzoxadiazolyl and the like; 3 to 6-membered monocyclic heteroaromatic groups containing 1 to 2 sulfur atoms and 1 to 3 nitrogen atoms, for example, thiazolyl, thiadiazolyl (for example, 1,2,4-thiadiazolyl, 1,3,4-thiadiazolyl, 1,2,5-thiadiazolyl and the like) and others; fused cyclic heteroaromatic groups containing 1 to 2 sulfur atoms and 1 to 3 nitrogen atoms, for example, benzothiazolyl, benzothiadiazolyl, imidazothiazolyl (for example, imidazo[2,1-b][1,3]thiazolyl and the like) and others; fused cyclic heteroaromatic groups containing 1 to 2 oxygen atoms, for example, benzofuranyl, dibenzo[b,d]furanyl and the like; fused cyclic heteroaromatic groups containing 1 to 2 sulfur atoms, for example, benzothienyl and the like; and others.

"Heterocyclic group" further refers to a 3 to 10-membered saturated or unsaturated cyclic group containing 1 to 4 heteroatoms selected from O, N and S, and preferable examples thereof include 3 to 7-membered saturated or unsaturated heteromonocyclic groups containing 1 to 4 nitrogen atoms, for example, pyrrolidinyl, pyrrolinyl, imidazolidinyl, piperidyl, piperazinyl, homopiperazinyl and the like; 3 to 10-membered saturated or unsaturated bicyclic heterocyclic groups containing 1 to 4 nitrogen atoms, for example, quinuclidinyl and the like; 3 to 6-membered saturated heteromonocyclic groups containing one oxygen atom, for example, 1H-tetrahydropyranyl, tetrahydrofuranyl and the like; 3 to 6-membered saturated or unsaturated heteromonocyclic groups containing 1 to 2 oxygen atoms and 1 to 3 nitrogen atoms, for example, morpholinyl, oxazolinyl (for example, 2-oxazolinyl and the like) and others; 3 to 6-membered saturated or unsaturated heteromonocyclic groups containing 1 to 2 sulfur atoms and 1 to 3 nitrogen atoms, for example, thiazolidinyl and others; and the like. "Heterocyclic group" further refers to a heterocyclic group in which an aryl group or a heteroaryl group is fused to a 3 to 10-membered saturated or unsaturated heterocyclic group containing 1 to 4 heteroatoms selected from O, N and S, and examples thereof includes isocromanyl, cromanyl, isoindolinyl, indolinyl, 3,4-dihydro-2H-1,4-benzoxazinyl, dihydrobenzofuranyl, 2,3-dihydro-1,4-benzodioxyzinyl and the like.

"Heteroaryl" refers to a group included in the "heterocyclic group" and having an aromaticity.

"Cycloalkyl" refers to a saturated hydrocarbon ring group containing 3 to 10 carbon atoms. For example, cyclopropyl, cyclobutyl, cyclopentyl, cyclohexyl, cycloheptyl, norbornyl, adamantyl and the like are included.

"Halogen" includes a fluorine atom, a chlorine atom, a bromine atom and an iodine atom and is preferably a fluorine atom, a chlorine atom or a bromine atom.

"Heteroaryl lower alkyl" refers to a lower alkyl substituted by the heteroaryl(s) described above, and includes, for example, thiazolyl lower alkyl (for example, thiazolylmethyl and the like) and others.

"Halogen-substituted lower alkyl" refers to a lower alkyl substituted by halogen atom(s). For example, fluoromethyl, chloromethyl, difluoromethyl, dichloromethyl, dibromomethyl, trifluoromethyl, trichloromethyl, fluoroethyl, chloroethyl, 2,2,2-trifluoroethyl, 2,2,2-trichloroethyl, 2,2,3,3,3-pentafluoroethyl, fluoropropyl, fluorobutyl, fluorohexyl and the like are included.

"Lower alkenyl" refers to an unsaturated linear or branched noncyclic hydrocarbon containing 2 to 10 carbon atoms and having at least one double bond. The number of carbon atoms is preferably 2 to 6. For example, vinyl, propenyl, butenyl, pentenyl, hexenyl and the like are included.

"Lower alkenylene" refers to a divalent group formed by removing a hydrogen atom from "lower alkenyl".

Examples of "acyl group" include carboxy; esterified carboxy; carbamoyl substituted by lower alkyl(s), aryl(s), aryl lower alkyl(s), arylsulfonyl(s), heterocyclic group-substituted sulfonyl(s), lower alkylsulfonyl(s) or heterocyclic group(s); substituted or unsubstituted arylsulfonyl; sulfonyl substituted by a heterocyclic group; lower alkylsulfonyl; cycloalkylcarbonyl; lower alkanoyl; substituted or unsubstituted aroyl;carbonyl substituted by a heterocyclic group, and the like.

Examples of the esterified carboxy group include substituted or unsubstituted lower alkyl-O—C(=O)— (for example, methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl and the like), substituted or unsubstituted aryl-O—C(=O)— (for example, phenoxycarbonyl, 4-nitrophenoxycarbonyl, 2-naphthyloxycarbonyl and the like), substituted or unsubstituted aryl lower alkyl-O—C(=O)— (for example, benzyloxycarbonyl, phenethyloxycarbonyl, benzhydryloxycarbonyl, 4-nitrobenzyloxycarbonyl and the like) and others.

Examples of the lower alkyl-substituted carbamoyl group include methylcarbamoyl, ethylcarbamoyl, propylcarbamoyl, dimethylcarbamoyl, diethylcarbamoyl, methylethylcarbamoyl and the like.

Examples of the aryl-substituted carbamoyl group include phenylcarbamoyl, naphthylcarbamoyl, lower alkyl-substituted phenylcarbamoyl (for example, tolylcarbamoyl, xylylcarbamoyl and the like) and others.

Examples of the aryl lower alkyl-substituted carbamoyl group include benzylcarbamoyl, phenethylcarbamoyl, phenylpropylcarbamoyl and the like.

Examples of the arylsulfonyl-substituted carbamoyl group include phenylsulfonylcarbamoyl, tolylsulfonylcarbamoyl and the like.

Examples of the (heterocyclic group-substituted sulfonyl)-substituted carbamoyl include pyridylsulfonylcarbamoyl and the like.

Examples of the lower alkylsulfonyl-substituted carbamoyl group include methylsulfonylcarbamoyl, ethylsulfonylcarbamoyl and the like.

Examples of the substituted or unsubstituted arylsulfonyl group include phenylsulfonyl, tolylsulfonyl, halophenylsulfonyl (for example, fluorophenylsulfonyl and the like) and others.

Examples of the heterocyclesulfonyl group include pyrrolidinylsulfonyl and the like.

Examples of the lower alkylsulfonyl group include methylsulfonyl, ethylsulfonyl and the like.

Examples of the cycloalkylcarbonyl group include cyclopropylcarbonyl, cyclobutylcarbonyl, cyclopentylcarbonyl or cyclohexylcarbonyl and the like.

Examples of the lower alkanoyl group include formyl, acetyl, propionyl, butyryl, isobutyryl, valeryl, isovaleryl, pivaloyl, hexanoyl and the like.

Examples of the substituted or unsubstituted aroyl group include benzoyl, naphtoyl, toluoyl, di(tert-butyl)benzoyl, halogen-substituted lower alkyl-O-benzoyl (for example, trifluoromethoxybenzoyl and the like) and others.

The heterocyclic group moiety of the "heterocyclic group-substituted carbonyl" refers to the "heterocyclic group" described above. For example, pyridylcarbonyl and the like are included.

"Mono-lower alkylamino" refers to an amino group substituted by a "lower alkyl" group described above. For example, methylamino, ethylamino, propylamino, isopropylamino, butylamino, isobutylamino, pentylamino, hexylamino and the like are included.

"Di-lower alkylamino" refers to an amino group substituted by two same or different "lower alkyl" groups described above. For example, dimethylamino, diethylamino, dipropylamino, diisopropylamino, dibutylamino, diisobutylamino, dipentylamino, dihexylamino, ethylmethylamino, methylpropylamino, butylmethylamino, ethylpropylamino, butylethylamino and the like are included.

Examples of "lower alkylenedioxy group" include methylenedioxy group, ethylenedioxy group and the like.

Examples of "appropriate substituent" include lower alkyl, halogen, cyano, lower alkenyl, halogen-substituted lower alkyl, lower alkyl-O—, cyano lower alkyl-O—, halogen-substituted lower alkyl-O—, aryl, heteroaryl, aryl-O—, heteroaryl-O—, aryl lower alkyl, acyl-O—, acyl, heteroaryl lower alkyl-O—, lower alkylthio, nitro, amino, hydroxy, mercapto, mono-lower alkylamino, di-lower alkylamino, acylamino, arylamino, carboxy and the like.

Although "aryl", "heteroaryl", "cycloalkyl", "heterocycle", "phenyl", "naphthyl", "benzothiazolyl", "cyclohexyl" and the like are described as monovalent groups in the present Description for convenience, they may be multivalent groups of divalent or higher according to their structures. The present invention encompasses these structures. For example, although groups exemplified for

[formula 19]

in formula (III) are described as monovalent groups for convenience, they are actually multivalent groups of divalent or higher. Specific aspects of the divalent group correspond to those having the suffix of the above ring groups converted into diyl in accordance with the Nomenclature of Organic Chemistry. For example, a divalent group corresponding to a phenyl group that is a monovalent group is a phenylene group. A divalent group corresponding to a benzothiazolyl group as a monovalent group is benzothiazolediyl.

A preferred aspect of the compound of formula (I) above as the compound of the present invention is compounds represented by the formula (II) and/or formula (III) above. Accordingly, all the compounds represented by formula (II) and/or formula (III) above are included in the compounds represented by formula (I) above. Further a preferred aspect of the compound of formula (II) above is compounds represented by formula (III) above. Preferred aspects of the compounds of formula (III) are shown below.

(1) A is lower alkylene which may be substituted by phenyl(s), lower alkylene-O— which may be substituted by phenyl(s), lower alkenylene or a bond, more preferably lower alkenylene or a bond, most preferably a bond.

[formula 20]

(2)

is phenyl, naphthyl, benzothiazolyl, dibenzo[b,d]furanyl, thienyl, pyrazolyl, benzothienyl, imidazolyl, pyridyl, 2,1,3,-benzothiadiazolyl, isoquinolyl, cyclopropyl, cyclohexyl or 3,4-dihydro-2H-1,4-benzoxazinyl, preferably phenyl, naphthyl, pyridyl or isoquinolyl, more preferably phenyl or naphthyl, most preferably phenyl.

(3) Ra, which is the same or different, is hydrogen, lower alkyl, halogen, cyano, lower alkenyl, halogen-substituted lower alkyl, lower alkyl-O—, cyano lower alkyl-O—, halogen-substituted lower alkyl-O—, phenyl, oxadiazolyl, phenoxy, pyridyloxy, pyridylcarbonyl, pyrrolidinylsulfonyl, thiazolyl lower alkyl-O—, lower alkylsulfonyl, nitro or di-lower alkylamino, in which the phenyl and oxadiazolyl and the phenyl, pyridyl and thiazolyl moieties of each of the phenoxy, pyridyloxy, pyridylcarbonyl and thiazolyl lower alkyl-O— may be substituted by lower alkyl(s), lower alkyl-O-(s) or halogen(s); more preferably, Ra, which is the same or different, is hydrogen, lower alkyl, halogen, cyano, halogen-substituted lower alkyl, lower alkyl-O—, halogen-substituted lower alkyl-O— or lower alkylsulfonyl, most preferably Ra, which is the same or different, is hydrogen or halogen.

(4) $R^2$ to $R^6$ are hydrogen, lower alkyl, lower alkyl-O—, benzyloxy, hydroxy, halogen, halogen-substituted lower alkyl, carboxy, or a lower alkylene dioxy group formed from any adjacent two groups of $R^3$ to $R^6$, in which at least one of $R^2$ to $R^6$ is carboxy; more preferably, $R^2$ to $R^6$ are hydrogen, lower alkyl, lower alkyl-O—, benzyloxy, hydroxy, halogen, halogen-substituted lower alkyl, carboxy, or a lower alkylene dioxy group formed from any adjacent two groups of $R^3$ to $R^6$, provided either one of $R^2$ or $R^5$ is carboxy; more preferably, $R^2$ is carboxy, and $R^3$ to $R^6$ are hydrogen, lower alkyl, lower alkyl-O—, benzyloxy, hydroxy, halogen, halogen-substituted lower alkyl, or a lower alkylene dioxy group formed from any adjacent two groups; most preferably, $R^2$ is carboxy, and $R^3$ to $R^6$ are hydrogen, lower alkyl, lower alkyl-O— or halogen.

(5) n is preferably an integer of 1 to 3.

Particularly preferred aspects of the compound of formula (III) are, for example, compounds composed of each preferred group described in (1) to (5) above in combination. Specifically, they are compounds composed of a combination described in (A1) to (A11) described below.

(A1) A compound wherein A is lower alkylene which may be substituted by phenyl(s), lower alkylene-O— which may be substituted by phenyl(s), lower alkenylene or a bond;

[formula 21]

is phenyl, naphthyl, benzothiazolyl, dibenzo[b,d]furanyl, thienyl, pyrazolyl, benzothienyl, imidazolyl, pyridyl, 2,1,3,-benzothiadiazolyl, isoquinolyl, cyclopropyl, cyclohexyl or 3,4-dihydro-2H-1,4-benzoxazinyl, and Ra, which is the same or different, is hydrogen, lower alkyl, halogen, cyano, lower alkenyl, halogen-substituted lower alkyl, lower alkyl-O—, cyano lower alkyl-O—, halogen-substituted lower alkyl-O—, phenyl, oxadiazolyl, phenoxy, pyridyloxy, pyridylcarbonyl, pyrrolidinylsulfonyl, thiazolyl lower alkyl-O—, lower alkylsulfonyl, nitro or di-lower alkylamino, in which the phenyl and oxadiazolyl and the phenyl, pyridyl and thiazolyl moieties of each of the phenoxy, pyridyloxy, pyridylcarbonyl and thiazolyl lower alkyl-O— may be substituted by lower alkyl(s), lower alkyl-O-(s) or halogen(s); $R^2$ to $R^6$ are hydrogen, lower alkyl, lower alkyl-O—, benzyloxy, hydroxy, halogen, halogen-substituted lower alkyl, carboxy, or a lower alkylene dioxy group formed from any adjacent two groups of $R^3$ to $R^6$, in which at least one of $R^2$ to $R^6$ is carboxy, and n is an integer of 1 to 3.

(A2) The compound described in (A1), wherein either one of $R^2$ or $R^5$ is necessarily carboxy.

(A3) The compound described in (A2) above, wherein A is lower alkenylene or a bond,

[formula 22]

is phenyl, naphthyl, pyridyl or isoquinolyl, $R^2$ is carboxy, Ra, which is the same or different, is hydrogen, lower alkyl, halogen, cyano, halogen-substituted lower alkyl, lower alkyl-O—, halogen-substituted lower alkyl-O— or lower alkylsulfonyl, $R^3$ to $R^6$ are hydrogen, lower alkyl, lower alkyl-O—, benzyloxy, hydroxy, halogen, halogen-substituted lower alkyl, or a lower alkylene dioxy group formed from any adjacent two groups of $R^3$ to $R^6$.

(A4) The compound described in (A3) above, wherein A is a bond,

[formula 23]

is phenyl, Ra, which is the same or different, is hydrogen or halogen, $R^3$ to $R^6$ are hydrogen, lower alkyl, lower alkyl-O— or halogen.

(A5) The compound described in (A4) above, wherein Ra is halogen.

(A6) The compound described in (A5) above, wherein $R^3$ to $R^5$ are hydrogen and $R^6$ is halogen.

(A7) The compound described in (A4) above, which is 1-[(4-bromophenyl)sulfonyl]-1H-indole-3-carboxylic acid, 4-methoxy-1-(phenylsulfonyl)-1H-indole-3-carboxylic acid, 5-methyl-1-(phenylsulfonyl)-1H-indole-3-carboxylic acid, 5-fluoro-1-(phenylsulfonyl)-1H-indole-3-carboxylic acid, 7-fluoro-1-(phenylsulfonyl)-1H-indole-3-carboxylic acid, 1-[(4-bromophenyl)sulfonyl]-7-chloro-1H-indole-3-carboxylic acid, 7-chloro-1-(phenylsulfonyl)-1H-indole-3-carboxylic acid or 5-chloro-1-(phenylsulfonyl)-1H-indole-3-carboxylic acid.

(A8) The compound described in (A1) above, wherein A is a bond,

[formula 24]

is phenyl or naphthyl, Ra, which is the same or different, is hydrogen, lower alkyl, halogen, cyano, halogen-substituted lower alkyl, lower alkyl-O—, halogen-substituted lower alkyl-O— or lower alkylsulfonyl, $R^3$ is carboxy, $R^2$ and $R^4$ to $R^6$ are hydrogen, lower alkyl, lower alkyl-O—, benzyloxy, hydroxy, halogen or halogen-substituted lower alkyl.

(A9) The compound described in (A1) above, wherein A is a bond,

[formula 25]

is phenyl or naphthyl, Ra, which is the same or different, is hydrogen, lower alkyl, halogen, cyano, halogen-substituted lower alkyl, lower alkyl-O—, halogen-substituted lower alkyl-O— or lower alkylsulfonyl, $R^4$ is carboxy, $R^2$ to $R^3$ and $R^5$ to $R^6$ are hydrogen, lower alkyl, lower alkyl-O—, benzyloxy, hydroxy, halogen or halogen-substituted lower alkyl.

(A10) The compound described in (A1) above, wherein A is a bond,

[formula 26]

is phenyl or naphthyl, Ra, which is the same or different, is hydrogen, lower alkyl, halogen, cyano, halogen-substituted lower alkyl, lower alkyl-O—, halogen-substituted lower alkyl-O— or lower alkylsulfonyl, $R^5$ is carboxy, $R^2$ to $R^4$ and $R^6$ are hydrogen, lower alkyl, lower alkyl-O—, benzyloxy, hydroxy, halogen or halogen-substituted lower alkyl.

(A11) The compound described in (A1) above, wherein A is a bond,

[formula 27]

is phenyl or naphthyl, Ra, which is the same or different, is hydrogen, lower alkyl, halogen, cyano, halogen-substituted lower alkyl, lower alkyl-O—, halogen-substituted lower alkyl-O— or lower alkylsulfonyl, $R^6$ is carboxy, $R^2$ to $R^5$ are hydrogen, lower alkyl, lower alkyl-O—, benzyloxy, hydroxy, halogen or halogen-substituted lower alkyl.

Other preferred aspects of the compound of formula (I), the compound of the present invention, are described below.

(B1) A compound, wherein L is a bond,

[formula 28]

is phenyl or naphthyl, $R^{222}$ is carboxy, Raaa, which is the same or different, is hydrogen or halogen, $R^{111}$, $R^{333}$, $R^{444}$, $R^{555}$ and $R^{666}$ are hydrogen, a double line of a solid line and a dotted line is a single bond, and p is an integer of 1 to 3.

(B2) A compound, wherein L is a bond,

[formula 29]

is phenyl, Raaa, which is the same or different, is hydrogen or halogen, $R^{111}$ is carboxy-substituted lower alkyl or carboxy-substituted lower alkenyl, $R^{222}$, $R^{333}$, $R^{444}$, $R^{555}$ and $R^{666}$ are hydrogen, a double line of a solid line and a dotted line is a double bond, and p is an integer of 1 to 3.

(B3) A compound, wherein L is a bond,

[formula 30]

is phenyl, Raaa, which is the same or different, is hydrogen or halogen, $R^{444}$ is carboxy-substituted lower alkyl or carboxy-substituted lower alkenyl, $R^{111}$, $R^{222}$, $R^{333}$, $R^{555}$ and $R^{666}$ are hydrogen, a double line of a solid line and a dotted line is a double bond and p is an integer of 1 to 3.

Examples of groups that form prodrugs of the compound of the present invention include the groups described in Prog. Med. 5: 2157-2161 (1985), the groups described in "Pharmaceutical Research and Development", Vol. 7, Drug Design, p. 163-198, 1990, Hirokawa Publishing Co., and the like. Especially, derivatives of the compound of the present invention in which a free carboxy group is converted into an amide or ester can be metabolized in vivo to be converted into the compound of the general formula (I) and/or (II) and/or (III), and these are considered to be the prodrugs of the present invention. These prodrugs are included in the present invention.

The compound of the present invention represented by formula (I) and/or formula (II) and/or formula (III) may have one or more asymmetric centers and may be present as enantiomers or diastereomers in this case. The present invention includes both of the mixture of isomers and the individual isomers separated.

The compound of the present invention represented by formula (I) and/or formula (II) and/or formula (III) may be present as tautomers, and the present invention includes both of the mixture of tautomers and the individual tautomers separated.

The compound of the present invention represented by formula (I) and/or formula (II) and/or formula (III) may be present as geometric isomers, and the present invention includes both of the mixture of geometric isomers and the individual geometric isomers separated.

The compound of the present invention represented by formula (I) and/or formula (II) and/or formula (III) may be converted into a salt thereof by an ordinary method. Preferred salts of the compound represented by formula (I) and/or formula (II) and/or formula (III) are pharmaceutically acceptable salts, and examples thereof include metal salts such as alkali metal salts (for example, sodium salt, potassium salt and the like), alkaline earth metal salts (for example, calcium salt, magnesium salt and the like), ammonium salt, organic base salts (for example, trimethylamine salt, triethylamine salt, pyridine salt, picoline salt, dicyclohexylamine salt and the like), organic acid salts (acetate, malonate, tartrate, methanesulfonate, benzenesulfonate, formate, toluenesulfonate, trifluoroacetate and the like), inorganic acid salts (hydrochloride, hydrobromide, sulfate, phosphate and the like), amino acid salts (alginate, aspartate, glutamate and the like) and others. Accordingly, the present invention encompasses all of the indole derivatives represented by formula (I) and/or formula (II) and/or formula (III) and pharmaceutically acceptable salts thereof.

The compound of formula (I) and/or formula (II) and/or formula (III) may form hydrates and various pharmaceutically acceptable solvates. These hydrates and solvates are also included in the present invention.

The present invention also encompasses radiolabeled derivatives of the compound of formula (I) and/or formula (II) and/or formula (III) that are useful for biological research.

(General Production Method)

The compound (I) and/or (II) and/or (III) as an active ingredient of the present invention can be produced by utilizing the characteristics based on the types of skeleton or substituent and by applying various known synthetic methods. It is sometimes effective, in terms of production techniques, that the functional group is protected by an appropriate protecting group or replaced by a group that can be readily converted into the functional group in the stage of a raw material to intermediate depending on the type of the functional group during the production. Examples of such functional group include an amino group, a hydroxy group, a carboxyl group and the like, and examples of such protecting group thereof include protecting groups described in "Protective Groups in Organic Synthesis", 3rd ed., 1999, T. W. Greene and P. G. M. Wuts. These protecting groups may be appropriately selected and used depending on the reaction conditions. By these methods, a desired compound can be obtained by introducing a protecting group, performing a reaction, and then removing the protecting group or converted the protecting group into a desired group, as required.

Further, a prodrug of the compound (I) and/or (II) and/or (III) or a pharmaceutically acceptable salt thereof can be produced by introducing a specific group, as in the protecting group above, in the stage of a raw material or intermediate to performing a reaction using a compound (I) and/or (II) and/or (III) obtained. The reaction can be performed by applying the methods known to the person skilled in the art, such as ordinary esterification, amidation and acylation.

(First Production Method)

According to the first production method, the compound of the present invention (III) is produced by a sulfonamide condensation reaction using a compound (IV) and/or compound (V). The compound of the present invention (I) and/or (II) can also be produced by a similar method.

Production can be performed by reacting a compound represented by general formula (IV) below:

[formula 31]

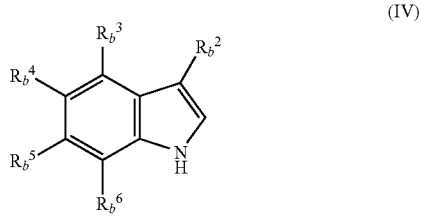

(IV)

(wherein, $Rb^2$ to $Rb^6$ represent hydrogen or an appropriate substituent, in which at least one of $Rb^2$ to $Rb^6$ represents a carboxy group that may be protected, and any adjacent two groups of $Rb^3$ to $Rb^6$ together may form a lower alkylene dioxy group) and a sulfonic acid or a reactive derivative thereof represented by general formula (V) below:

[formula 32]

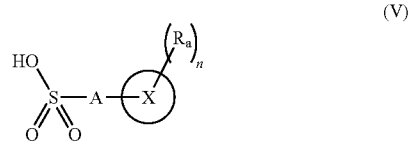

(V)

(wherein A, X, Ra and n are defined in formula (III) above). Examples of the reactive derivative of sulfonic acid include reactive derivatives generally used, such as sulfonyl halides and sulfonic anhydride, and sulfonyl halides are particularly preferred.

The solvent used in this reaction is not particularly limited, as long as the solvent does not inhibit the reaction and dissolves the starting materials in a certain level, and the solvent may be, for example, aliphatic hydrocarbons such as hexane, cyclohexane, heptane, ligroin or petroleum ether; aromatic hydrocarbons such as benzene, toluene or xylene; halogenated hydrocarbons such as dichloromethane, chloroform, carbon tetrachloride, 1,2-dichloroethane, chlorobenzene or dichlorobenzene; ethers such as diethyl ether, diisopropyl ether, tetrahydrofuran, dioxane, dimethoxyethane, diethylene glycol dimethyl ether, tert-butyl methyl ether or cyclopentyl methyl ether; nitro compounds such as nitromethane; nitriles such as acetonitrile or isobutyronitrile; amides such as formamide, N,N-dimethylformamide, N,N-dimethylacetamide or N-methyl-2-pyrrolidinone; or sulfoxides such as dimethyl sulfoxide or sulfolane, and is preferably ethers and amides, particularly preferably tetrahydrofuran.

The base used in this reaction may be, for example, alkali metal carbonates such as sodium carbonate, potassium carbonate or lithium carbonate; alkali metal hydrogen carbonates such as sodium hydrogen carbonate, potassium hydrogen carbonate or lithium hydrogen carbonate; alkali metal acetates such as sodium acetate; alkali metal hydrides such as lithium hydride, sodium hydride or potassium hydride; alkali metal hydroxides such as sodium hydroxide, potassium hydroxide or lithium hydroxide; alkali metal alkoxides such as sodium methoxide, sodium ethoxide, potassium tert-butoxide or lithium methoxide; organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); alkyllithiums such as methyllithium, ethyllithium or n-butyllithium; or lithium alkylamides such as lithium diisopropylamide or lithium dicyclohexylamide, and is preferably alkali metal hydrides (in particular, lithium hydride or sodium hydride), metal alkoxides (in particular, sodium methoxide, potassium tert-butoxide) or alkyllithiums (in particular, n-butyllithium).

The reaction temperature of this reaction is generally −78° C. to 100° C., preferably −78° C. to 50° C., depending on the raw material compounds, reagents and the like.

The reaction time of this reaction is generally 5 minutes to 24 hours, preferably 10 minutes to 12 hours, depending on the raw material compounds, reagents and the reaction temperature.

When at least one of $Rb^2$ to $Rb^6$ represents a protected carboxy group in the formula (IV) above, the compound (III) of the present invention can be obtained by deprotecting the protecting group after the reaction above.

Preferable protecting groups for the carboxy group in the "carboxy which may be protected" and deprotection methods therefor are described in "Protective Groups in Organic Synthesis" (3rd Edition, T. W. Greene and P. GM. Wuts, John Wiley & Sons, Inc.), and the like, and the entire description thereof is herein incorporated. Examples of the protecting group for a carboxy group include esters, amides, ortho-esters and the like. The deprotection method therefor can be performed in accordance with conventional methods, for example, hydrolysis, reduction and the like.

(Second Production Method)

The compound of the present invention (I) and/or (II) and/or (III) having various functional group(s) can also be produced by methods per se well known to the person skilled in the art or known methods, or variations thereof. For example, a desired compound can be produced by a reaction forming an indole ring or subjecting a compound obtained by the production method described above to a substituent-modification reaction. Representative reactions are shown below.

(1) Indole Cyclization Reaction

The compound (I) and/or (II) and/or (III) can be produced using a benzene derivative having a nitro group as a raw material by a reaction forming an indole ring. It can be performed, for example, referring to the method described in Tetrahedron Letters 1989, 30 (16), 2129-2132.

(2) Oxidation

The compound (I) and/or (II) and/or (III) having a carboxyl group, a sulfonyl group or a sulfenyl group can be produced from a compound having an aldehyde group or a sulfide group by an oxidation reaction. The reaction can be performed referring, for example, to the methods described in Heterocycles 1987, 26(5), 1173-1176, "Experimental Chemistry Series", the Chemical Society of Japan ed., Maruzen, vol. 23, 4th ed., 1992 and vol. 17, 5th. ed., 2005 or the "Compendium of Organic Synthetic Methods" described above, vols. 1 to 3, and the like.

(3) Alkylation

The compound (I) and/or (II) and/or (III) having a lower alkoxy group or a lower alkylamino group can be produced by subjecting a compound having a hydroxy group or an amino group to an alkylation reaction. For example, the reaction can be performed by the methods described in "Experimental Chemistry Series", the Chemical Society of Japan ed., Maruzen, vol. 20, 4th ed., 1992 and vol. 14, 5th ed., 2005, the "Compendium of Organic Synthetic Methods" described above, vols. 1 to 3, or the like.

(4) Amination and Alkoxylation Reactions by Substitution Reaction

The compounds (I) and/or (II) and/or (III) having a lower alkoxy group or a lower alkylamino group can also be produced by substituting a compound having halogen with a corresponding alcohol or amine compound in a basic condition. For the reaction, the reaction conditions described in "Experimental Chemistry Series", the Chemical Society of Japan ed., Maruzen, vol. 20, 4th ed., 1992 and vol. 14, 5th ed., 2005, may be appropriately selected for use.

(5) Amidation and Esterification

The compound (I) and/or (II) and/or (III) having an amide group or an ester group can be produced by reacting a compound having an amino group or a hydroxy group as a raw material with a carboxylic acid or a reactive derivative thereof. The reaction can be performed referring, for example, to the methods described in "Experimental Chemistry Series", the Chemical Society of Japan ed., Maruzen, vol. 22, 4th ed., 1992 and vol. 16, 5th ed., 2005, the "Compendium of Organic Synthetic Methods" described above, vols. 1 to 3, or the like.

(6) Others

The compound (I) and/or (II) and/or (III) having an $\alpha$, $\beta$-unsaturated carboxyl group can be produced by a method using Wittig reaction or Horner-Emmons reaction of a compound having an aldehyde group followed by hydrolysis of the ester or by Knoevenagel reaction. The production can be conducted referring, for example, to the method described in "Experimental Chemistry Series", the Chemical Society of Japan ed., Maruzen, vol. 19, 4th ed., 1992 and vol. 13, 5th ed., 2005, "Comprehensive Organic Synthesis", vol. 2, Pergamon Press, 1991, or the like.

(Production Method for Raw Material Compound)

Of the raw material compounds for the First Production Method above, the raw material compound (IV) in which $Rb^2$ is carboxy can be produced in accordance with a method (1) in which carboxylic acid is introduced in one step, for example, the method described in Bioorganic and Medicinal Chemistry Letters 2005, 15, 2734-2737; a method (2) in which oxidation reaction is performed after introduction of an aldehyde group, for example, the method described in Journal of the Chemical Society 1954, 3842-3845 and Heterocycles 1987, 26(5), 1173-1176; a method (3) in which an ester is hydrolyzed; and the like.

In production of the raw material compounds for the First Production Method and/or Second Production Method above, the substitution method can be performed referring to the method described in "Experimental Chemistry Series", the Chemical Society of Japan ed., Maruzen, vol. 23, 4th ed., 1992 and the like, hydrolysis to the method described in "Experimental Chemistry Series", the Chemical Society of Japan ed., Maruzen, vol. 22, 4th ed., 1992 and the like, and deprotection to the method in "Protective Groups in Organic Synthesis", 3rd ed., 1999 described above.

The compound (I) and/or (II) and/or (III) thus produced can be isolated and purified in its free form or as a salt thereof by a general salt formation reaction. Isolation and purification are conducted applying general chemical operations such as extraction, concentration, distillation, crystallization, filtration, recrystallization, various chromatographic operations and the like.

Various isomers can be isolated by an ordinary method utilizing the differences in physicochemical properties among the isomers. For example, optical isomers can be isolated and purified by a method in which a racemic compound is converted to a diasteromer salt with an optically active organic acid (tartaric acid and the like) followed by fractional crystallization, or by a technique in which column chromatography using a chiral column and the like. In addition, an optically active compound may also be produced using a suitable optically active compound as a raw material. Here, a mixture of diasteromers can be separated by fractional crystallization or chromatography and the like.

EXAMPLE

The production methods for compounds included in the compound (I) and/or (II) and/or (III) as an active ingredient of the present invention will be described below as Examples. Production methods for the novel compounds used as raw materials will be described as Production Examples. The production methods for the compound (I) and/or (II) and/or (III) are not limited to the production methods in specific Examples shown below and the compound of the present invention can be produced by a combination of these production methods or known production methods.

The following abbreviations are used in Production Examples, Examples and Tables below.

Ex: Example No., REx: Production Example No., Data: physicochemical data (FAB+:FAB–MS $(M+H)^+$, FAB–: FAB–MS $(M-H)^-$, ESI+:ESI–MS $(M+H)^+$, ESI–:ESI–MS $(M-H)^-$, API+:API–ES–MS $(M+H)^+$, EI:EI–MS $(M)^+$, NMR–DMSOd6: $\delta$(ppm) of characteristic peak(s) in $^1H$ NMR in DMSO-$d_6$), Str: Structural formula, DME: dimethoxyethane, DMF: N,N-dimethylformamide, DMSO: dimethyl sulfoxide, THF: tetrahydrofuran, MeCN: acetonitrile, MeOH: methanol, tBuOH: t-butyl alcohol, n-BuLi: n-butyllithium, RT: retention time (minutes) in HPLC, Ps: position of substitution with —COOH.

Production Example 1

To a solution of 3.0 g of 7-ethylindole in 25 mL of DMF, 3.5 mL of trifluoroacetic anhydride was added under ice cooling and the resulting mixture was stirred at room temperature for 3 hours. To the solution, 100 mL of water was added, and the precipitated solid was collected by filtration. The solid thus obtained was suspended in 100 mL of 5 M aqueous sodium hydroxide solution and the resulting suspension was stirred at 100° C. for 5 hours. After the solution was allowed to cool, it was washed twice with 30 mL of 1,2-dichloroethane. Concentrated hydrochloric acid was added to the aqueous layer to adjust the pH to pH2 and the precipitated solid was collected by filtration and washed with ether to obtain 3.14 g of 7-ethylindole-3-carboxylic acid as a beige solid.

The compounds listed in Table 1 were obtained by the method similar to that described in Production Example 1.

TABLE 1

| REx | Str | Data |
|---|---|---|
| 1 | 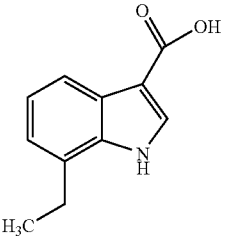 | FAB−: 188 |
| 2 | 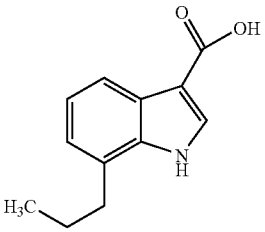 | FAB+: 204 |
| 3 | 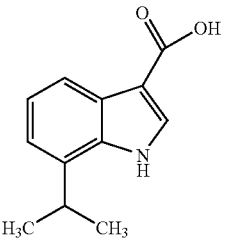 | EI: 203 |
| 4 | 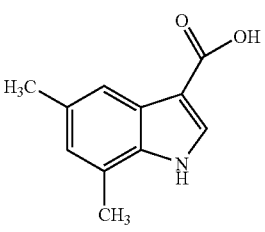 | EI: 189 |
| 5 | 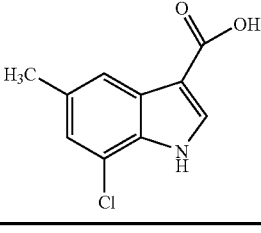 | FAB−: 208 |

Production Example 6

To 4.5 mL of DMF cooled in an ice-salt bath, 1.3 mL of phosphorus oxychloride was added, and the resulting mixture was stirred for 30 minutes. A solution of 2.13 g of 7-chloro-4-methyl-1H-indole in 3 mL of DMF was added to the solution under cooling and the resulting mixture was stirred at room temperature for 15 minutes and at 35° C. for 1 hour. After the solution was allowed to cool, 20 g of ice and 15 mL of 10 M aqueous sodium hydroxide solution were added, the resulting mixture was heated to 100° C., then allowed to cool to room temperature, and stirred under ice cooling for 30 minutes, and the precipitated solid was collected by filtration. To a solution of the solid obtained in 15 mL of MeCN and 50 mL of t-BuOH, 14 mL of 2-methyl-2-butene and 3.1 g of sodium dihydrogen phosphate were added, and a mixture of 9.3 g of sodium chlorite and 15 mL of water were further added, and the resulting mixture was stirred at room temperature for 2 days. To the solution, 100 mL of toluene and 50 mL water were added, and the mixture was extracted twice with 50 mL of 0.5 M aqueous sodium hydroxide solution. Concentrated hydrochloric acid was added to the extract to adjust the pH to pH3, the precipitated solid was collected by filtration, and the obtained solid was purified by silica gel column chromatography (chloroform-methanol=100:1 →150:1→20:1) to obtain 0.79 g of 7-chloro-4-methyl-1H-indole-3-carboxylic acid as a beige solid.

The compounds listed in Table 2 were obtained by the method similar to that described in Production Example 6.

TABLE 2

| REx | Str | Data |
|---|---|---|
| 6 | 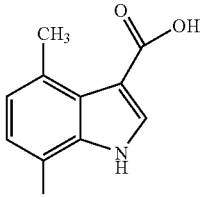 | EI: 209 |
| 7 | 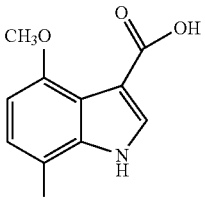 | EI: 181 |
| 8 | 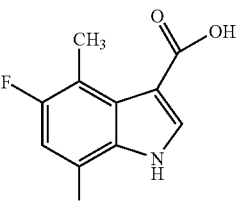 | EI: 227 |
| 9 |  | FAB−: 246 |

Production Example 10

To a solution of 1.01 g of methyl 5-(trifluoromethyl)-1H-indole-3-carboxylate in 12 mL of MeOH and 12 mL of THF, 6 mL of 1 M aqueous sodium hydroxide solution was added, and the resulting mixture was stirred at 80° C. overnight. To the solution, 3 mL of 1 M aqueous sodium hydroxide solution was further added, and the resulting mixture was stirred at 80°

C. for 6 hours. To the solution, 9 mL of 1 M hydrochloric acid and 60 mL of water were added, the precipitated solid was collected by filtration, and the solid obtained was purified by silica gel column chromatography (chloroform-methanol=100:1 →150:1→20:1) and then washed with hexane to obtain 0.71 g of 5-(trifluoromethyl)-1H-indole-3-carboxylic acid as a cream-colored solid. FAB−: 228

Production Example 11

A solution of 5.21 g of 1-chloro-4-methyl-2-nitrobenzene in 150 mL of THF was cooled to −50° C. To the solution was added 95 mL of 1 M vinylmagnesium bromide solution in THF while the inner temperature was kept at −30° C. or lower, and the resulting mixture was stirred at −50° C. for 2 hours. To the solution, 100 mL of the saturated aqueous ammonium chloride solution and 100 mL of 1 M hydrochloric acid were added, then the resulting mixture was warmed to room temperature and stirred for 15 minutes, and then extracted twice with 100 mL of ethyl acetate. The extract was washed with water and saturated aqueous sodium chloride solution and dried over anhydrous sodium sulfate, and then the solvent was evaporated under reduced pressure. The residue was purified by silica gel column chromatography (ethyl acetate-hexane=1:9) to obtain 2.69 g of 7-chloro-4-methylindole as a brown oil.

Compounds listed in Table 3 were obtained by the method similar to that described in Production Example 11.

TABLE 3

| REx | Str | Data |
|-----|-----|------|
| 11 | CH₃, Cl (indole) | EI: 165 |
| 12 | CH₃O, Cl (indole) | EI: 181 |
| 13 | CH₃, F, Cl (indole) | EI: 183 |
| 14 | F, Cl, Cl (indole) | EI: 202 |

The following Examples are described to explain the present invention in more detail, and the present invention will not restricted by the following Examples. Although the present invention is fully explained by way of the Examples, the person skilled in the art will appreciate that various alterations and modifications can naturally be made. Accordingly, these alterations and modifications are included in the present invention unless they depart from the scope of the present invention.

Example 1

4.8 mg of indole-3-carboxylic acid was dissolved in 1 mL of tetrahydrofuran, 0.042 mL of n-butyllithium (1.58 M hexane solution) was added to the solution at 0° C., the resulting mixture was stirred for 30 minutes. Then 5.3 mg of benzenesulfonyl chloride was added to the mixture, and the resulting mixture was stirred at 0° C. overnight. Water and chloroform were added to the mixture, the organic layer was separated and concentrated under reduced pressure, and the residue was purified by HPLC to obtain 1.0 mg of 1-(phenylsulfonyl)-1H-indole-3-carboxylic acid.

The HPLC conditions used for the purification will be described below.

Column: SunFire (registered trademark)

Particle size: 5 μm, Inner diameter: 19 mm, Length: 100 mm

Mobile phase: Solution A (=A sol), methanol

Solution B (B sol), 0.1% aqueous formic acid solution

TABLE 4

| Time(min) | A sol (%) | B sol (%) |
|-----------|-----------|-----------|
| 0-1 | 10 | 90 |
| 1-9 | 10→95 | 90→5 |
| 9-12 | 95 | 5 |

Flow rate: 25 mL/min

Column temperature: 20° C.

Injection volume: 800 IL

Example Compounds listed in Tables 6 to 22 below were obtained by the method similar to that described in Example 1. The conditions of HPLC performed for the determination of RT in Examples 1 to 132 are shown below.

Column: Wakosil-II 5C18AR (registered trademark)

Particle size: 5 μm, Inner diameter: 2.0 mm, Length: 30 mm

Mobile phase: Solution A (=A sol), 5 mM aqueous trifluoroacetic acid solution

Solution B (=B sol), methanol

TABLE 5

| Time(min) | A sol (%) | B sol (%) |
|-----------|-----------|-----------|
| 0-4 | 90→0 | 10→100 |
| 4-4.5 | 0 | 100 |

Flow rate: 1.2 mL/min

Detection wavelength: 254 nm

Column temperature: 35.0° C.

Injection volume: 5 μL

TABLE 6
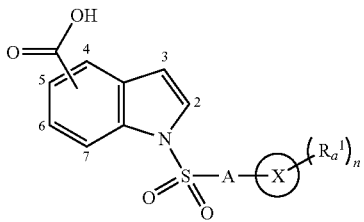
| Ex | Ps | —A—X(Rₐ¹)ₙ | RT | ESI+ |
|----|----|----|----|----|
| 1 | 3 | 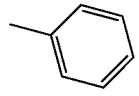 | 2.6 | 302 |
| 2 | 3 | 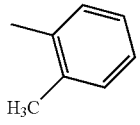 | 2.74 | 316 |
| 3 | 3 | 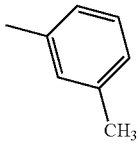 | 2.8 | 316 |
| 4 | 3 | 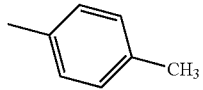 | 2.8 | 316 |
| 5 | 3 | 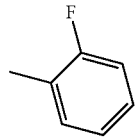 | 2.59 | 320 |
| 6 | 3 | 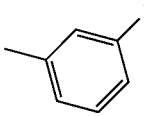 | 2.75 | 320 |
| 7 | 3 | 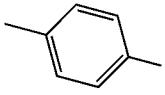 | 2.67 | 320 |
| 8 | 3 | 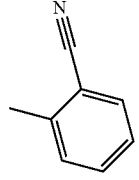 | 2.37 | 327 |
TABLE 7
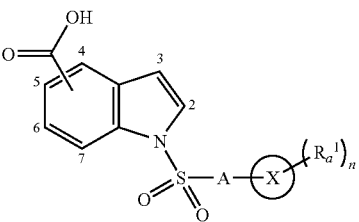
| Ex | Ps | —A—X(Rₐ¹)ₙ | RT | ESI+ |
|----|----|----|----|----|
| 9 | 3 | 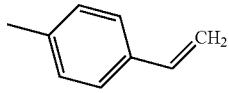 | 2.92 | 328 |
| 10 | 3 | 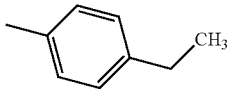 | 2.98 | 330 |
| 11 | 3 | 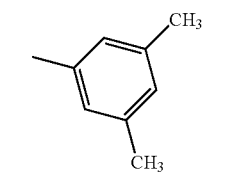 | 3 | 330 |
| 12 | 3 | 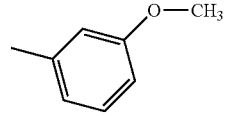 | 2.77 | 332 |
| 13 | 3 | 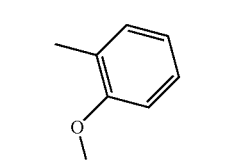 | 2.58 | 332 |
| 14 | 3 | 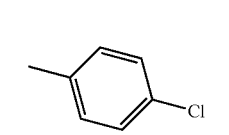 | 2.9 | 336 |
| 15 | 3 | 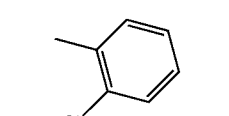 | 2.65 | 336 |
| 16 | 3 | 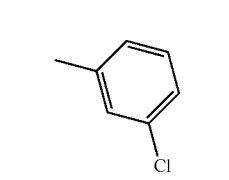 | 2.95 | 336 |

TABLE 8

| Ex | Ps | —A—X(Ra¹)n | RT | ESI+ |
|---|---|---|---|---|
| 17 | 3 | 2,6-difluorophenyl-methyl | 2.64 | 338 |
| 18 | 3 | 3,4-difluorophenyl-methyl | 2.83 | 338 |
| 19 | 3 | 4-isopropylphenyl-methyl | 3.13 | 344 |
| 20 | 3 | 4-butylphenyl-methyl | 3.34 | 358 |
| 21 | 3 | 4-(isopropoxy)phenyl-methyl | 3.03 | 360 |
| 22 | 3 | 4-(trifluoromethyl)phenyl-methyl | 3.03 | 370 |
| 23 | 3 | 3,4-dichlorophenyl-methyl | 3.21 | 370 |
| 24 | 3 | 4-(2-cyanoethoxy)phenyl-methyl | 2.52 | 371 |

TABLE 9

| Ex | Ps | —A—X(Ra¹)n | RT | ESI+ |
|---|---|---|---|---|
| 25 | 3 | 4-biphenyl-methyl | 3.22 | 378 |
| 26 | 3 | 3-biphenyl-methyl | 3.25 | 378 |
| 27 | 3 | 2-biphenyl-methyl | 2.95 | 378 |
| 28 | 3 | 4-bromophenyl-methyl | 2.95 | 380 |
| 29 | 3 | 4-(trifluoromethoxy)phenyl-methyl | 3.07 | 386 |
| 30 | 3 | 4'-methyl-4-biphenyl-methyl | 3.42 | 392 |
| 31 | 3 | 4-phenoxyphenyl-methyl | 3.23 | 394 |
| 32 | 3 | 3-phenoxyphenyl-methyl | 3.23 | 394 |

TABLE 10
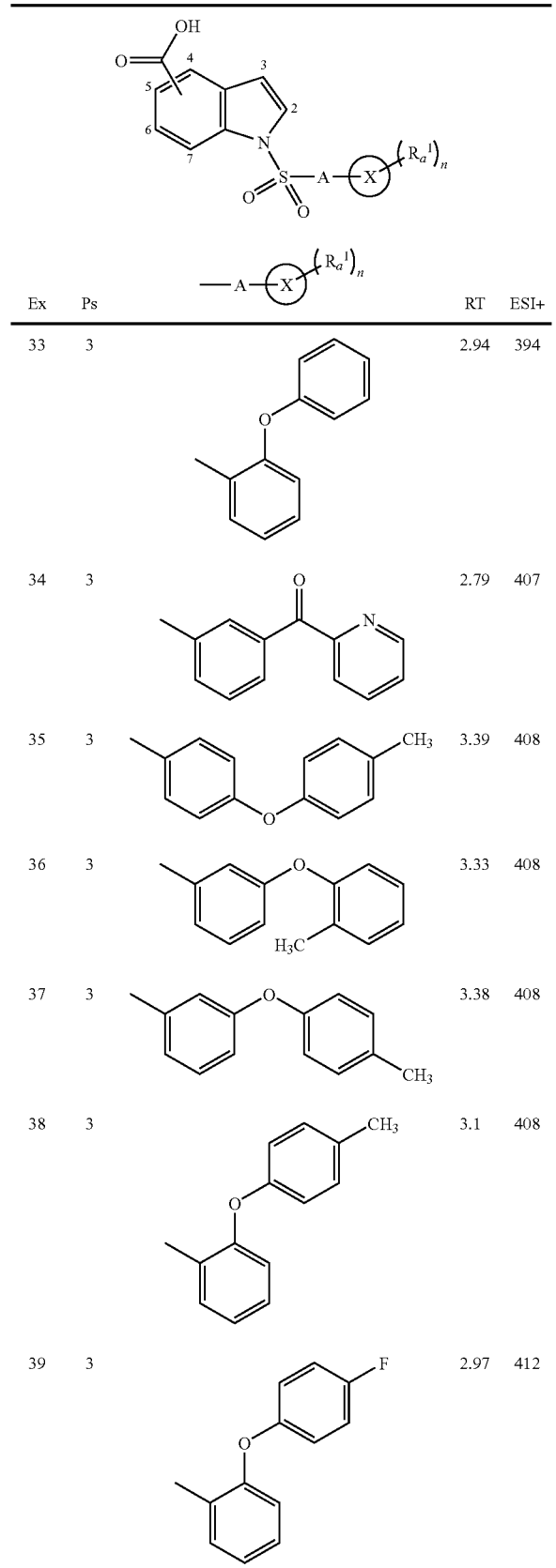
TABLE 10-continued
TABLE 11
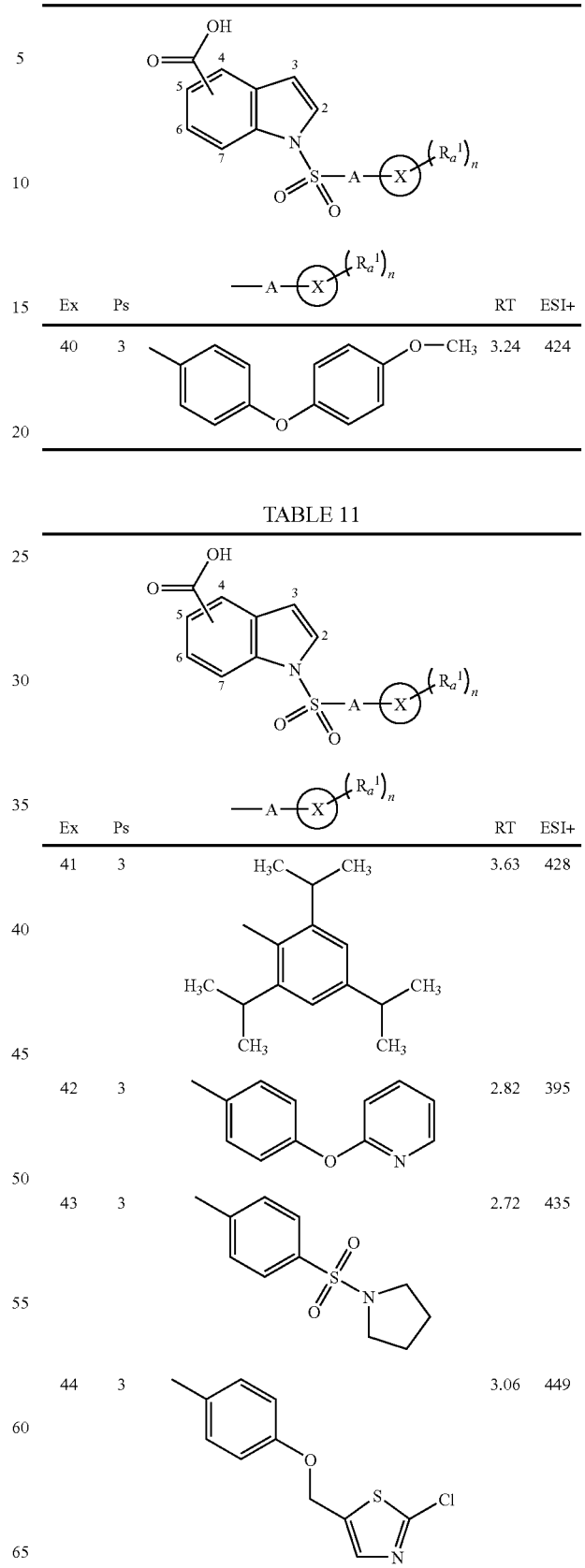

TABLE 11-continued

[Structure: indole with COOH at position 4/5 and N-SO2-A-(X)-(Ra1)n substituent]

| Ex | Ps | —A—(X)(Ra1)n | RT | ESI+ |
|---|---|---|---|---|
| 45 | 3 | 3,5-difluorophenyl-methyl | 2.84 | 338 |
| 46 | 3 | 3-(2-methoxyphenoxy)phenyl-methyl | 3.15 | 424 |
| 47 | 3 | 3-(4-fluorophenoxy)phenyl-methyl | 3.23 | 412 |
| 48 | 3 | 2,4-difluorophenyl-methyl | 2.68 | 338 |

TABLE 12

[Structure: indole with COOH at position 4/5 and N-SO2-A-(X)-(Ra1)n substituent]

| Ex | Ps | —A—(X)(Ra1)n | RT | ESI+ |
|---|---|---|---|---|
| 49 | 3 | 2'-methyl-4-methoxybiphenyl | 3 | 408 |
| 50 | 3 | 3-methyl-4'-methoxybiphenyl | 3.28 | 408 |
| 51 | 3 | 2-methyl-4'-chlorobiphenyl | 3.09 | 412 |
| 52 | 3 | 3-methyl-4'-fluorobiphenyl | 3.26 | 396 |
| 53 | 3 | 3-methyl-4'-methylbiphenyl | 3.44 | 392 |
| 54 | 3 | 2'-methyl-4-methylbiphenyl | 3.12 | 392 |
| 55 | 3 | 2-fluoro-4,5-dimethylphenyl | 2.96 | 334 |
| 56 | 3 | 2,4-dichloro-5-methylphenyl | 2.98 | 370 |

TABLE 13

[Structure: indole-3-carboxylic acid with N-sulfonyl-A-X(Ra¹)n substituent]

| Ex | Ps | —A—X—(Ra¹)n | RT | ESI+ |
|---|---|---|---|---|
| 57 | 3 | 3-chloro-4-fluoro-methylphenyl | 3.02 | 354 |
| 58 | 3 | methyl-nitro-trifluoromethylphenyl | 2.91 | 415 |
| 59 | 3 | methoxy-methylphenyl (CH3, OCH3) | 2.76 | 346 |
| 60 | 3 | chloro-dimethylphenyl | 3.13 | 350 |
| 61 | 3 | methyl-nitrophenyl | 2.5 | 347 |
| 62 | 3 | methyl-trifluoromethylphenyl | 2.81 | 370 |
| 63 | 3 | trimethylphenyl | 2.96 | 330 |
| 64 | 3 | methyl-dichlorophenyl | 2.91 | 370 |

TABLE 14

[Structure: indole-3-carboxylic acid with N-sulfonyl-A-X(Ra¹)n substituent]

| Ex | Ps | —A—X—(Ra¹)n | RT | ESI+ |
|---|---|---|---|---|
| 65 | 3 | methyl-dichlorophenyl | 3.06 | 370 |
| 66 | 3 | dimethyl-methoxyphenyl | 2.79 | 346 |
| 67 | 3 | chloro-methyl-methoxyphenyl | 3.02 | 366 |
| 68 | 3 | dimethyl-chlorophenyl | 3.07 | 350 |
| 69 | 3 | dimethyl-chlorophenyl | 2.8 | 350 |
| 70 | 3 | methyl-propylphenyl | 3.17 | 344 |
| 71 | 3 | methyl-difluorophenyl | 2.79 | 338 |
| 72 | 3 | methyl-trifluoromethylphenyl | 3.06 | 370 |

TABLE 15

Structure: indole-2,3,4,5,6,7 with 4-COOH and N1-SO2-A-(X)-(Ra1)n

| Ex | Ps | —A—(X)—(Ra1)n | RT | ESI+ |
|----|----|----|----|----|
| 73 | 3 | 2-methyl-4-fluorophenyl | 2.92 | 334 |
| 74 | 3 | 2-methyl-4-fluoro-5-chlorophenyl | 2.99 | 354 |
| 75 | 3 | 3-methyl-2-fluoro-... chlorophenyl | 2.87 | 354 |
| 76 | 3 | 2-CF3-4-NO2 phenyl (methyl) | 3.11 | 415 |
| 77 | 3 | 2,3-dimethyl-5-fluorophenyl | 2.85 | 334 |
| 78 | 3 | 3-methyl-4-methoxy-ethylphenyl | 2.98 | 360 |
| 79 | 3 | 1-naphthyl | 2.92 | 352 |
| 80 | 3 | 2-naphthyl | 3.04 | 352 |

TABLE 16

Structure: indole-2,3,4,5,6,7 with 4-COOH and N1-SO2-A-(X)-(Ra1)n

| Ex | Ps | —A—(X)—(Ra1)n | RT | ESI+ |
|----|----|----|----|----|
| 81 | 3 | 1,4-dimethylnaphthyl | 3.07 | 366 |
| 82 | 3 | (dimethylamino)naphthyl | 3.1 | 395 |
| 83 | 3 | methylbenzothiazolyl | 2.57 | 359 |
| 84 | 3 | methyl-N-methyl-benzoxazine | 2.84 | 373 |
| 85 | 3 | 2-methyl-5-methyl-1,3,4-oxadiazole-phenyl | 2.52 | 384 |
| 86 | 3 | methyldibenzofuranyl | 3.31 | 392 |
| 87 | 3 | 3-methylthiophenyl | 2.46 | 308 |
| 88 | 3 | 3,4-dimethyl-5-chloro-1-methylpyrazolyl | 2.63 | 354 |

TABLE 17
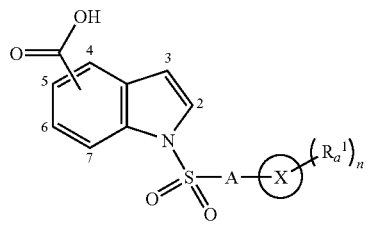
| Ex | Ps | —A—(X)(Ra¹)n | RT | ESI+ |
|---|---|---|---|---|
| 89 | 3 | (2-benzothiophenyl) | 3.08 | 358 |
| 90 | 3 | (1,2-dimethylimidazol-4-yl) | 1.86 | 320 |
| 91 | 3 | (3-benzothiophenyl) | 2.86 | 358 |
| 92 | 3 | (3-pyridyl) | 2.28 | 303 |
| 93 | 3 | (benzo[1,2,5]thiadiazol-4-yl) | 2.57 | 360 |
| 94 | 3 | (5-chloro-2-thienyl) | 2.99 | 342 |
| 95 | 3 | (1,3,4,5-tetramethylpyrazol-?-yl) | 2.42 | 334 |
| 96 | 3 | (4,5-dichloro-2-thienyl) | 3.32 | 375 |
TABLE 18
| Ex | Ps | —A—(X)(Ra¹)n | RT | ESI+ |
|---|---|---|---|---|
| 97 | 3 | —CH₂—(3-CF₃-C₆H₄) | 2.76 | 384 |
| 98 | 3 | —CH₂—(4-CF₃-C₆H₄) | 2.85 | 384 |
| 99 | 3 | —CH₂—(2-pyridyl) | 2 | 317 |
| 100 | 3 | —CH₂—(3,4-dichlorophenyl) | 2.88 | 384 |
| 101 | 3 | —CH₂—(4-Cl-C₆H₄) | 2.73 | 350 |
| 102 | 3 | —CH₂—(4-F-C₆H₄) | 2.54 | 334 |
| 103 | 3 | —CH(Et)—(2-Cl, phenyl-substituted) | 2.98 | 440 |
| 104 | 3 | —CH₂—C₆H₅ | 2.52 | 316 |

TABLE 19
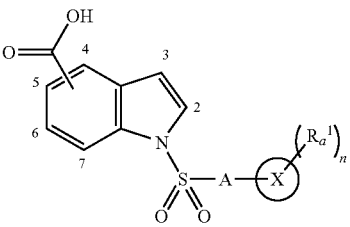
| Ex | Ps | –A–(X)(Ra¹)n | RT | ESI+ |
|---|---|---|---|---|
| 105 | 3 | 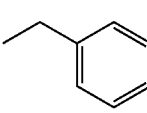 | 2.39 | 361 |
| 106 | 3 | 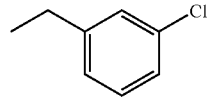 | 2.7 | 350 |
| 107 | 3 | 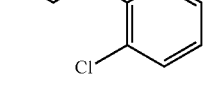 | 2.92 | 364 |
| 108 | 3 | 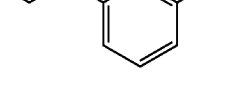 | 2.84 | 364 |
| 109 | 3 | 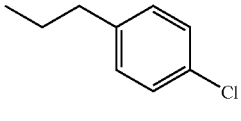 | 2.84 | 364 |
| 110 | 3 | 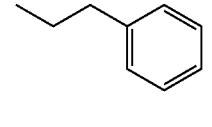 | 2.71 | 330 |
| 111 | 3 | 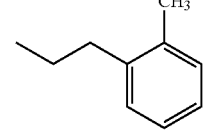 | 2.93 | 344 |
| 112 | 3 | 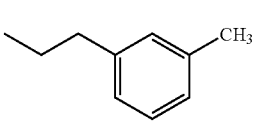 | 2.86 | 344 |
TABLE 20
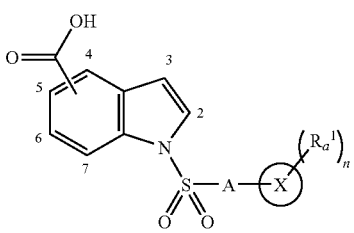
| Ex | Ps | –A–(X)(Ra¹)n | RT | ESI+ |
|---|---|---|---|---|
| 113 | 3 | 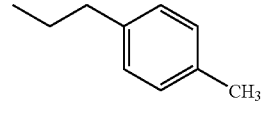 | 2.88 | 344 |
| 114 | 3 | 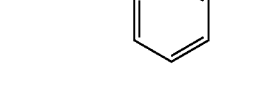 | 2.69 | 348 |
| 115 | 3 | 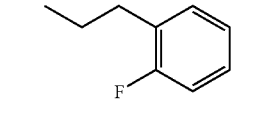 | 2.73 | 348 |
| 116 | 3 | 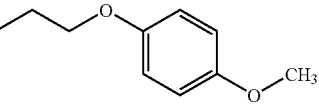 | 2.81 | 390 |
| 117 | 3 | 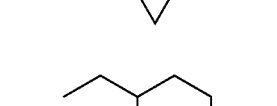 | 2.22 | 266 |
| 118 | 3 | 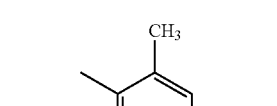 | 3.04 | 322 |
| 119 | 4 | 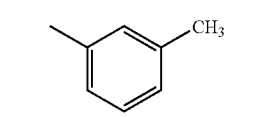 | 2.71 | 316 |
| 120 | 4 |  | 2.73 | 316 |

TABLE 21

[Structure: indole-carboxylic acid with N-sulfonyl-A-(X)(Ra¹)n substituent, positions labeled 2,3,4,5,6,7]

| Ex | Ps | —A—(X)(Ra¹)n | RT | ESI+ |
|---|---|---|---|---|
| 121 | 4 | 4-methylbiphenyl | 3.16 | 378 |
| 122 | 4 | 5-methyl-1-(N,N-dimethylamino)naphthalene | 3.02 | 395 |
| 123 | 5 | 5-methyl-1-(N,N-dimethylamino)naphthalene | 2.97 | 395 |
| 124 | 6 | methylphenyl | 2.43 | 302 |
| 125 | 6 | 2,3-dimethylphenyl | 2.61 | 316 |
| 126 | 6 | 3,5-dimethylphenyl | 2.61 | 316 |
| 127 | 6 | 2,5-dimethylphenyl | 2.61 | 316 |
| 128 | 6 | 1-methylnaphthalene | 2.8 | 352 |

TABLE 22

[Structure: indole-carboxylic acid with N-sulfonyl-A-(X)(Ra¹)n substituent]

| Ex | Ps | —A—(X)(Ra¹)n | RT | ESI+ |
|---|---|---|---|---|
| 129 | 6 | 2-methylnaphthalene | 2.86 | 352 |
| 130 | 6 | 4-methylbiphenyl | 3.14 | 378 |
| 131 | 6 | 4-methyl-bromophenyl | 2.75 | 380 |
| 132 | 6 | 5-methyl-1-(N,N-dimethylamino)naphthalene | 2.97 | 395 |

TABLE 23

| Ex | NMR-DMSOd6 |
|---|---|
| 28 | 7.36-7.46 (2H, m), 7.85 (2H, d), 8.00 (1H, d), 8.06-8.11 (3H, m), 8.37 (1H, s), 13.03 (1H, br) |
| 80 | 7.33-7.45 (2H, m), 7.70-7.78 (2H, m), 8.02-8.07 (4H, m), 8.13 (1H, d), 8.26 (1H, d), 8.44 (1H, s), 9.01 (1H, d), 13.00 (1H, br) |

Example 133

To a solution of 300 mg of 1H-indole-3-carboxylic acid in 9 mL of THF, 2.68 mL of 1.60 M n-BuLi hexane solution was added dropwise while the inner temperature was kept at −50° C. or lower by cooling in a dry ice-acetone bath, and the resulting mixture was stirred at the same temperature for 5 minutes, then at 0° C. for 1 hour. The solution was cooled in a dry ice-acetone bath and a solution of 461 mg of 4-methoxybenzenesulfonyl chloride in 1 mL of THF was added dropwise. The solution was stirred at 0° C. for 3 hours. To the solution, 20 mL of 5% aqueous potassium hydrogen sulfate solution and 40 mL of water were added in this order, and then the resulting mixture was extracted with ethyl acetate. The organic layer was washed with saturated aqueous sodium chloride solution and dried over anhydrous magnesium sulfate, and then the solvent was evaporated under reduced pressure. To the residue was added 5 mL of ethyl acetate, and the resulting mixture was stirred at room temperature for 15 minutes. The white crystals formed were collected by filtration to obtain 509 mg of 1-[(4-methoxyphenyl)sulfonyl]-1H-indole-3-carboxylic acid as a white solid.

Example compounds listed in Tables 24 to 31 below were obtained by the methods similar to that described in Example 133.

TABLE 24

| Ex | Str |
|---|---|
| 133 | *1-[(4-methoxyphenyl)sulfonyl]-1H-indole-3-carboxylic acid* |
| 134 | *1-[(3-methoxyphenyl)sulfonyl]-1H-indole-3-carboxylic acid* |
| 135 | *1-[(4-trifluoromethoxyphenyl)sulfonyl]-1H-indole-3-carboxylic acid* |
| 136 | *1-[(2-methylphenyl)sulfonyl]-1H-indole-3-carboxylic acid* |

TABLE 24-continued

| Ex | Str |
|---|---|
| 137 | *1-[(3-methylphenyl)sulfonyl]-1H-indole-3-carboxylic acid* |
| 138 | *1-[(4-methylphenyl)sulfonyl]-1H-indole-3-carboxylic acid* |
| 139 | *1-[(4-ethylphenyl)sulfonyl]-1H-indole-3-carboxylic acid* |
| 140 | *1-[(4-butylphenyl)sulfonyl]-1H-indole-3-carboxylic acid* |
| 141 | *1-[(4-tert-butylphenyl)sulfonyl]-1H-indole-3-carboxylic acid* |

TABLE 24-continued
| Ex | Str |
|---|---|
| 142 | 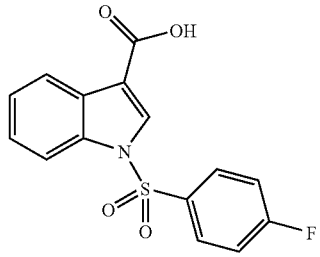 |
TABLE 25
| Ex | Str |
|---|---|
| 143 | 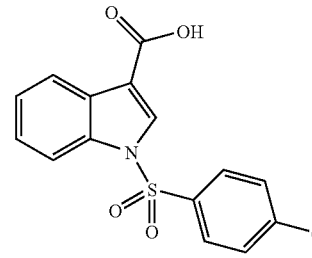 |
| 144 | 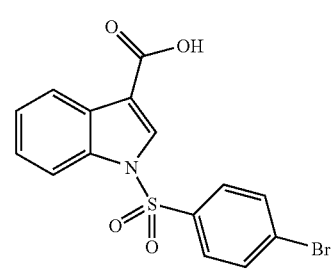 |
| 145 | 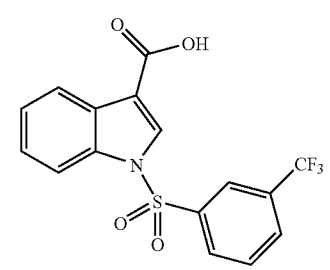 |
| 146 | 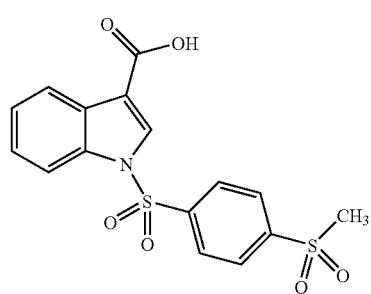 |
TABLE 25-continued
| Ex | Str |
|---|---|
| 147 | 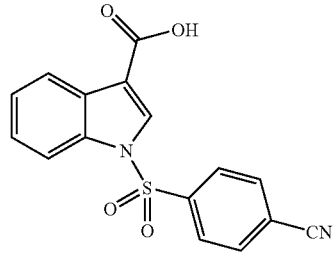 |
| 148 | |
| 149 | 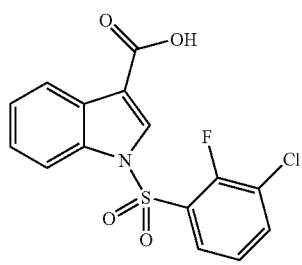 |
| 150 | 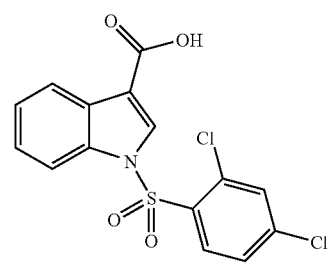 |
| 151 | 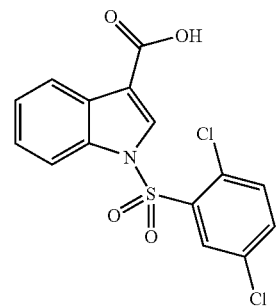 |

TABLE 25-continued
| Ex | Str |
|---|---|
| 152 | 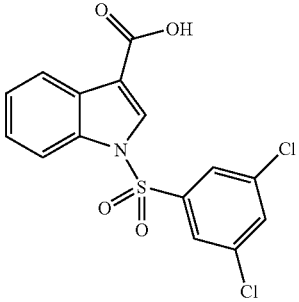 |
TABLE 26
| Ex | Str |
|---|---|
| 153 | 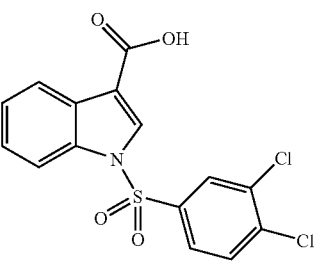 |
| 154 | 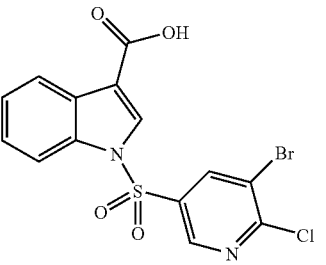 |
| 155 | 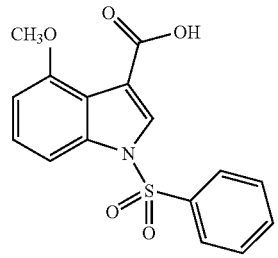 |
| 156 | 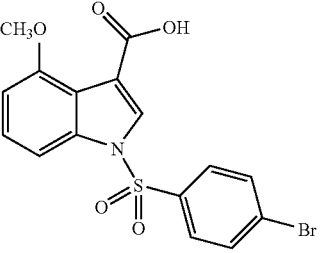 |
TABLE 26-continued
| Ex | Str |
|---|---|
| 157 | 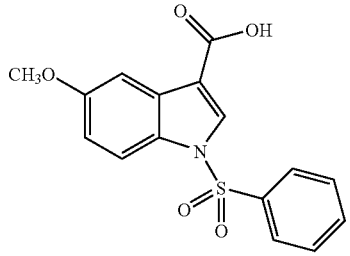 |
| 158 | 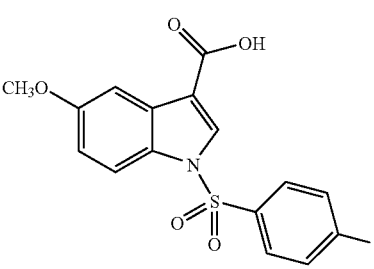 |
| 159 |  |
| 160 | 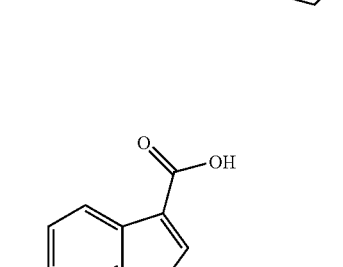 |
| 161 | 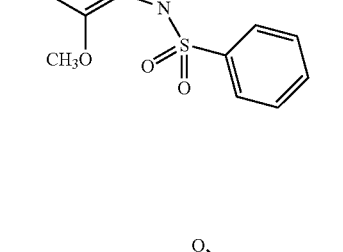 |

TABLE 26-continued
| Ex | Str |
|---|---|
| 162 | 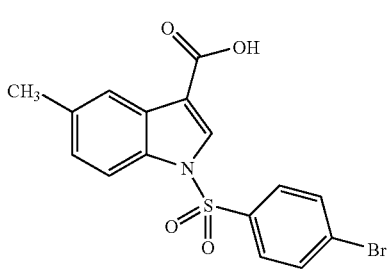 |
TABLE 27
| Ex | Str |
|---|---|
| 163 | 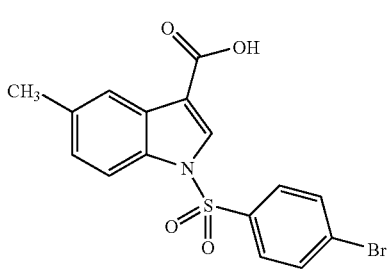 |
| 164 | 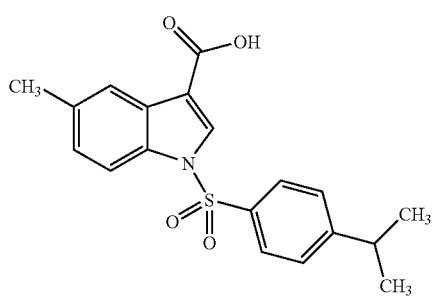 |
| 165 | 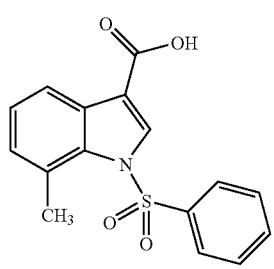 |
| 166 | 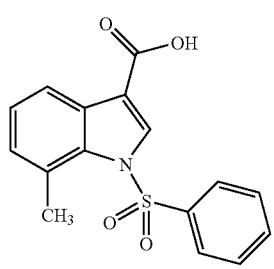 |
TABLE 27-continued
| Ex | Str |
|---|---|
| 167 | 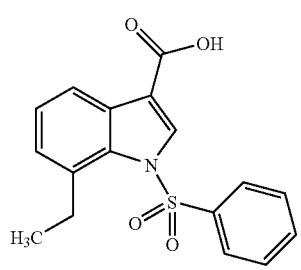 |
| 168 | 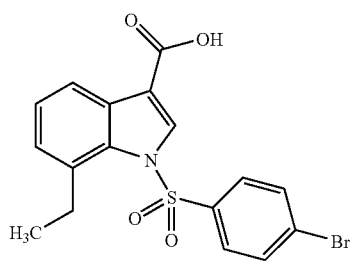 |
| 169 | 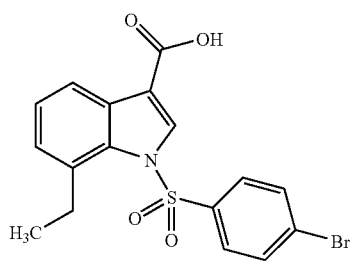 |
| 170 | 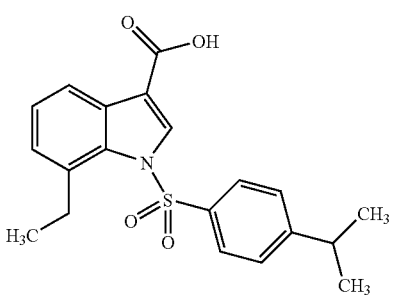 |
| 171 | 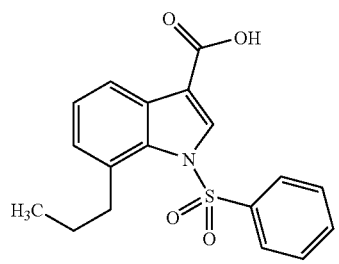 |

TABLE 27-continued
| Ex | Str |
|---|---|
| 172 | 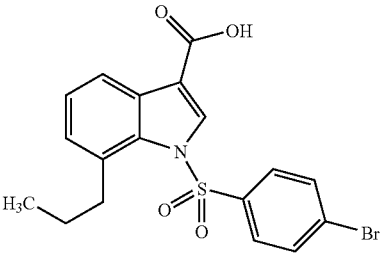 |
TABLE 28
| Ex | Str |
|---|---|
| 173 | 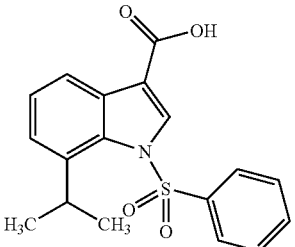 |
| 174 | 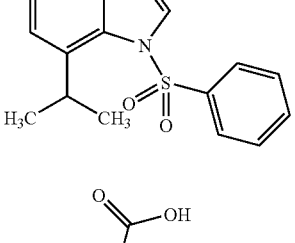 |
| 175 | 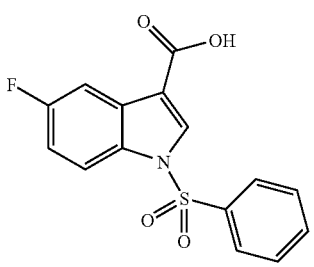 |
| 176 | 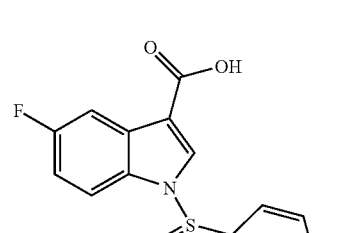 |
TABLE 28-continued
| Ex | Str |
|---|---|
| 177 | 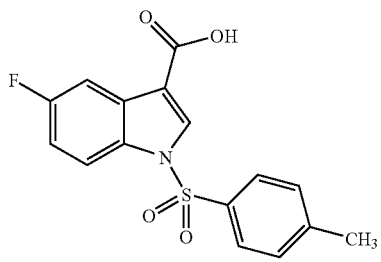 |
| 178 | 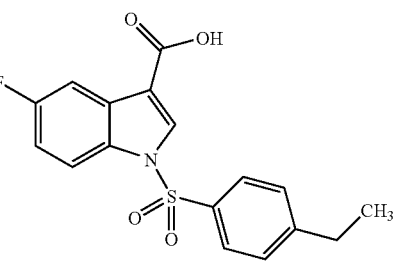 |
| 179 | 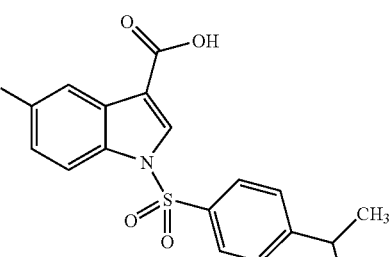 |
| 180 | 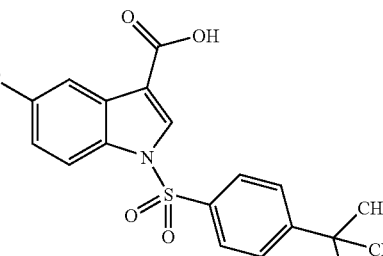 |
| 181 | 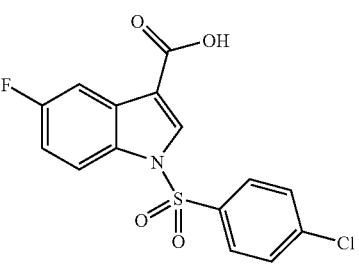 |

TABLE 28-continued

| Ex | Str |
| --- | --- |
| 182 | 5-fluoro-1-(4-bromo-2-methylphenylsulfonyl)-1H-indole-3-carboxylic acid |

TABLE 29

| Ex | Str |
| --- | --- |
| 183 | 5-fluoro-1-(4-bromo-2-fluorophenylsulfonyl)-1H-indole-3-carboxylic acid |
| 184 | 5-fluoro-1-(2,4-dichlorophenylsulfonyl)-1H-indole-3-carboxylic acid |
| 185 | 5-fluoro-1-(isoquinolin-5-ylsulfonyl)-1H-indole-3-carboxylic acid |
| 186 | 5-fluoro-1-((E)-styrylsulfonyl)-1H-indole-3-carboxylic acid |

TABLE 29-continued

| Ex | Str |
| --- | --- |
| 187 | 7-fluoro-1-(phenylsulfonyl)-1H-indole-3-carboxylic acid |
| 188 | 7-fluoro-1-(4-bromophenylsulfonyl)-1H-indole-3-carboxylic acid |
| 189 | 7-fluoro-1-(4-isopropylphenylsulfonyl)-1H-indole-3-carboxylic acid |
| 190 | 5-chloro-1-(phenylsulfonyl)-1H-indole-3-carboxylic acid |
| 191 | 7-chloro-1-(phenylsulfonyl)-1H-indole-3-carboxylic acid |

TABLE 29-continued
| Ex | Str |
|---|---|
| 192 | 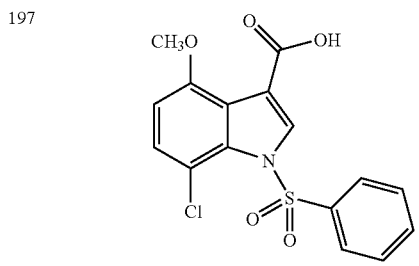 |
TABLE 30
| Ex | Str |
|---|---|
| 193 | |
| 194 | 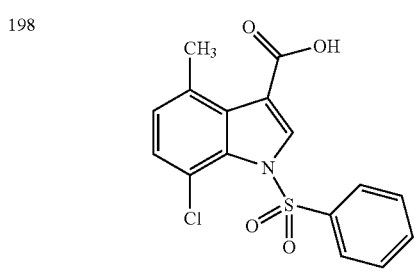 |
| 195 | |
| 196 | 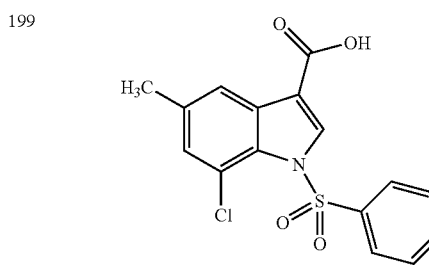 |
TABLE 30-continued
| Ex | Str |
|---|---|
| 197 | |
| 198 | 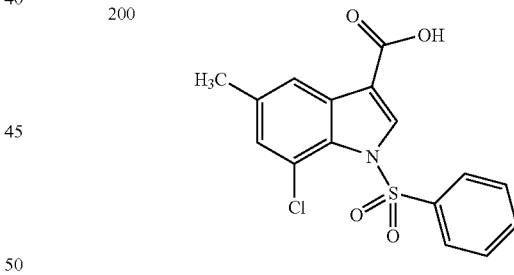 |
| 199 | |
| 200 | 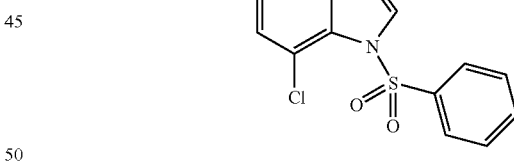 |
TABLE 31
| Ex | Str |
|---|---|
| 201 | 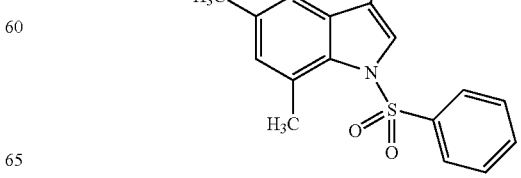 |

TABLE 31-continued

| Ex | Str |
|---|---|
| 202 | (5-carboxy-methylenedioxy-indole with N-phenylsulfonyl) |
| 203 | (5-carboxy-methylenedioxy-indole with N-(4-bromophenyl)sulfonyl) |
| 204 | (4-methyl-5-fluoro-7-chloro-indole-3-carboxylic acid with N-phenylsulfonyl) |
| 205 | (5-chloro-4-fluoro-7-chloro-indole-3-carboxylic acid with N-phenylsulfonyl) |
| 206 | (6-(2-carboxyvinyl)-indole with N-(4-bromophenyl)sulfonyl) |
| 207 | (5-(2-carboxyvinyl)-indole with N-(4-bromophenyl)sulfonyl) |

TABLE 31-continued

| Ex | Str |
|---|---|
| 208 | (4,5,6,7-tetrahydroindole-3-carboxylic acid with N-(4-bromophenyl)sulfonyl) |

TABLE 32

| Ex | Data |
|---|---|
| 133 | NMR-DMSOd6: 3.81 (3H, s), 7.12 (2H, d, J=9.0 Hz), 7.35-7.45 (2H, m), 7.96-8.11 (4H, m), 8.34 (1H, s), 12.97 (1H, s) ESI+: 332 |
| 134 | ESI+: 332 |
| 135 | ESI+: 386 |
| 136 | ESI+: 316 |
| 137 | ESI+: 316 |
| 138 | NMR-DMSOd6: 2.34 (3H, s), 7.35-7.44 (4H, m), 7.95-8.07 (4H, m), 8.34 (1H, s), 12.99 (1H, s) ESI+: 316 |
| 139 | ESI+: 330 |
| 140 | ESI+: 358 |
| 141 | ESI+: 358 |
| 142 | ESI+: 320 |
| 143 | ESI+: 336 |
| 144 | NMR-DMSOd6: 7.36-7.46 (2H, m), 7.85 (2H, d, J=8.8 Hz), 8.00 (1H, d, J=7.6 Hz), 8.06-8.11 (3H, m), 8.37 (1H, s), 13.03 (1H, s) FAB−: 378 |
| 145 | ESI−: 368 |
| 146 | ESI+: 380 |
| 147 | ESI−: 325 |
| 148 | ESI+: 350 |
| 149 | ESI+: 354 |
| 150 | API+: 370 |
| 151 | ESI+: 370 |
| 152 | ESI+: 370 |
| 153 | ESI+: 370 |
| 154 | ESI+: 417 |

TABLE 33

| Ex | Data |
|---|---|
| 155 | NMR-DMSOd6: 3.81 (3H, s), 6.79 (1H, d, J=8.2 Hz), 7.35 (1H, t, J=8.2 Hz), 7.5-7.8 (4H, m), 8.08 (2H, m), 8.14 (1H, s), 12.62 (1H, s) FAB+: 332 |
| 156 | ESI+: 411 |
| 157 | FAB: 330 |
| 158 | ESI−: 409 |
| 159 | FAB−: 330 |
| 160 | FAB+: 332 |
| 161 | FAB+: 408 |
| 162 | ESI−: 484, 486 |
| 163 | NMR-DMSOd6: 2.39 (3H, s), 7.24 (1H, d, J=8.6 Hz), 7.61 (2H, m), 7.73 (1H, m), 7.85 (2H, m), 8.11 (2H, m), 8.30 (1H, s), 12.97 (1H, s) ESI−: 314 |
| 164 | ESI−: 392 |
| 165 | FAB−: 356 |
| 166 | FAB−: 314 |
| 167 | ESI−: 392, 394 |

TABLE 33-continued

| Ex | Data |
|---|---|
| 168 | NMR-DMSOd6: 0.86 (3H, t, J=7.3 Hz), 2.89 (2H, q, J=7.3 Hz), 7.20 (1H, d, J=7.1 Hz), 7.33 (1H, m), 7.66 (2H, m), 7.78 (1H, m), 7.87 (2H, m), 8.03 (1H, dd, J=0.7, 7.8 Hz), 8.42 (1H, s), 12.98 (1H, s) FAB−: 328 |
| 169 | ESI−: 406, 408 |
| 170 | FAB−: 370 |
| 171 | ESI−: 342 |
| 172 | FAB−: 420, 422 |
| 173 | FAB−: 342 |
| 174 | ESI−: 420, 422 |

TABLE 34

| Ex | Data |
|---|---|
| 175 | NMR-DMSOd6: 7.30 (1H, m), 7.6-7.8 (4H, m), 8.01 (1H, m), 8.16 (2H, m), 8.45 (1H, s), 13.12 (1H, s) ESI−: 318 |
| 176 | ESI−: 396, 398 |
| 177 | FAB−: 332 |
| 178 | FAB−: 346 |
| 179 | ESI−: 360 |
| 180 | ESI−: 374 |
| 181 | ESI−: 352 |
| 182 | ESI−: 410 |
| 183 | ESI−: 414 |
| 184 | ESI−: 386 |
| 185 | ESI+: 371 |
| 186 | FAB−: 344 |
| 187 | NMR-DMSOd6: 7.22 (1H, m), 7.36 (1H, m), 7.68 (2H, m), 7.79 (1H, m), 7.94 (1H, d, J=8.1 Hz), 8.07 (2H, d, J=7.3 Hz), 8.44 (1H, s), 13.15 (1H, s) FAB+: 320 |
| 188 | ESI−: 396 |
| 189 | ESI−: 360 |
| 190 | NMR-DMSOd6: 7.48 (1H, m), 7.65 (2H, m), 7.78 (1H, m), 8.01 (2H, d, J=8.4 Hz), 8.15 (2H, m), 8.44 (1H, s), 13.17 (1H, s) ESI−: 334 |
| 191 | NMR-DMSOd6: 7.39 (2H, m), 7.65 (2H, m), 7.80 (1H, m), 7.99 (2H, m), 8.16 (1H, dd, J=6.8, 2.2 Hz), 8.52 (1H, s), 13.17 (1H, s) ESI−: 333 |
| 192 | NMR-DMSOd6: 7.41 (2H, m), 7.87 (2H, m), 7.96 (2H, m), 8.16 (1H, dd, J=7.1, 2.1 Hz), 8.52 (1H, s), 13.17 (1H, s) ESI−: 413 |

TABLE 35

| Ex | Data |
|---|---|
| 193 | NMR-DMSOd6: 1.20 (6H, d, J=6.8 Hz), 2.96-3.04 (1H, m), 7.35-7.42 (2H, m), 7.53 (2H, d, J=8.5 Hz), 7.93 (2H, d, J=8.8 Hz), 8.15 (1H, dd, J=7.6, 1.7 Hz), 8.52 (1H, s), 13.17 (1H, s) ESI+: 378 |
| 194 | NMR-DMSOd6: 2.44 (3H, s), 7.39-7.45 (2H, m), 7.68 (1H, dd, J=8.0, 2.0 Hz), 7.77 (1H, d, J=8.4 Hz), 7.82 (1H, d, J=1.6 Hz), 8.18 (1H, dt, J=9.2, 2.4 Hz), 8.47 (1H, s), 13.22 (1H, s) FAB+: 429 |
| 195 | ESI−: 368 |
| 196 | ESI−: 446, 448 |
| 197 | ESI+: 366 |
| 198 | ESI−: 348 |
| 199 | FAB−: 348 |
| 200 | ESI−: 426, 428 |
| 201 | FAB+: 330 |
| 202 | FAB−: 344 |

TABLE 35-continued

| Ex | Data |
|---|---|
| 203 | NMR-DMSOd6: 6.10 (2H, s), 7.40 (1H, s), 7.48 (1H, s), 7.86 (2H, d, J=8.0 Hz), 8.09 (2H, d, J=8.0 Hz), 8.20 (1H, s), 12.97 (1H, s) ESI−: 422, 424 |
| 204 | ESI−: 366 |
| 205 | FAB−: 385 |
| 206 | FAB+: 407 |
| 207 | FAB+: 407 |
| 208 | NMR-DMSOd6: 1.57-1.67 (4H, m), 2.53-2.63 (4H, m), 7.76 (1H, s), 7.88-7.94 (4H, m), 12.48 (1H, s) ESI−: 382, 384 |

Example 209

To a solution of 1.0 g of 7-benzyloxy-1-phenylsulfonyl-1H-indole-3-carboxylic acid in 5 mL of trifluoroacetic acid, 1.0 g of 1,2,3,4,5-pentamethylbenzene was added, and the resulting mixture was stirred at room temperature overnight. 20 mL of ether was added to the solution, insoluble matter was removed, the solvent was evaporated under reduced pressure, and the residue was washed with ethyl acetate to obtain 0.25 g of 7-hydroxy-1-phenylsulfonyl-1H-indole-3-carboxylic acid as a gray solid. FAB−:316

Example 210 a) Ethyl 1-[(4-bromophenyl)sulfonyl]-1H-indole-2-carboxylate

To a solution of 0.5 g of potassium t-butoxide and 0.1 g of 18-crown-6 in 3 mL of THF, a mixed solution of 0.7 g of ethyl 1H-indole-2-carboxylate and 3 mL of THF was added, and the resulting mixture was stirred at room temperature for 30 minutes. The solution was cooled with ice, 1.13 g of 4-bromobenzenesulfonyl chloride was added, and the resulting mixture was stirred at room temperature for 5 hours. To the solution was added 60 mL of ethyl acetate, the resulting mixture was washed with water and saturated aqueous sodium chloride solution and dried over anhydrous sodium sulfate, and then the solvent was evaporated under reduced pressure. The residue was purified by silica gel column chromatography (ethyl acetate-hexane=1:5) to obtain 1.44 g of ethyl 1-[(4-bromophenyl)sulfonyl]-1H-indole-2-carboxylate as a pale yellow syrup. FAB+: 408, 410 b) {1-[(4-bromophenyl)sulfonyl]-11H-indol-2-yl}methanol

To a solution of 1.4 g of ethyl 1-[(4-bromophenyl)sulfonyl]-1H-indole-2-carboxylate in 10 mL of THF, 7.6 mL of diisobutylalminum hydride-toluene solution was added at a temperature of −60° C. or lower, and the resulting mixture was stirred under cooling in a dry ice-acetone bath for 5 hours and under ice cooling for 2 hours. After the solution was cooled to −70° C., 5 g of sodium sulfate decahydrate and 5 mL of methanol were added, the resulting mixture was warmed to room temperature, 50 mL of ethyl acetate and anhydrous sodium sulfate were added, insoluble matter was removed by filtration, and the solvent was evaporated under reduced pressure. The residue was purified by silica gel column chromatography (chloroform) to obtain 0.97 g of {1-[(4-bromophenyl)sulfonyl]-1H-indol-2-yl}methanol as a pale violet solid. EI: 365, 367 c) 1-[(4-bromophenyl)sulfonyl]-1H-indole-2-carbaldehyde

To a solution of 0.93 g of {1-[(4-bromophenyl)sulfonyl]-1H-indol-2-yl}methanol and 1.1 mL of triethylamine in 10 mL of 1,2-dichloroethane, a solution of 1.21 g of sulfur trioxide-pyridine complex in 5 mL of DMSO was added under ice cooling, and the resulting mixture was stirred under ice cooling for 1 hour. The solution was poured into a mixed solution of 25 ml of ice water and 25 mL of saturated aqueous sodium chloride solution, the resulting mixture was extracted with 100 mL of ethyl acetate, the extract was washed with 5% aqueous potassium hydrogen sulfate solution, water and saturated aqueous sodium chloride solution and dried over anhydrous sodium sulfate, and the solvent was evaporated under reduced pressure. The residue was washed with hexane to obtain 0.91 g of 1-[(4-bromophenyl)sulfonyl]-1H-indole-2-carbaldehyde as a beige solid. FAB+: 364, 366 d) (2E)-3-{1-[(4-bromophenyl)sulfonyl]-1H-indol-2-yl}acrylic Acid

To a solution of 0.41 g of 1-[(4-bromophenyl)sulfonyl]-1H-indole-2-carbaldehyde in 3 mL of pyridine, 0.35 g of malonic acid and 0.02 mL of piperidine were added, and the resulting mixture was stirred at 80° C. for 3 hours. After the solution was allowed to cool, 50 mL of water and concentrated hydrochloric acid were added to adjust the pH to pH3, and the precipitated solid was collected by filtration and washed with ethanol to obtain 0.29 g of (2E)-3-{1-[(4-bromophenyl)sulfonyl]-1H-indol-2-yl} acrylic acid as a pale yellow solid.

Example compounds listed in Table 36 below were obtained by the method similar to that of Example 210.

TABLE 36

| Ex | Str |
|---|---|
| 210 | 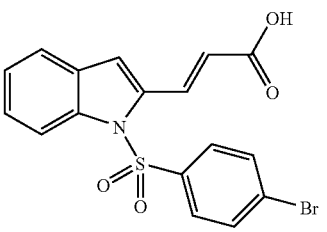 |
| 211 | 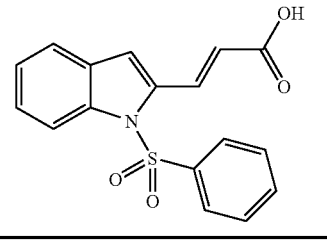 |

TABLE 37

| Ex | Data |
|---|---|
| 210 | NMR-DMSOd6: 6.59 (1H, d, J=15.9 Hz), 7.33 (1H, m), 7.44 (1H, m), 7.52 (1H, s), 7.62 (3H, m), 7.80 (2H, d, J=7.1 Hz), 8.09 (1H, d, J=8.5 Hz), 8.17 (1H, d, J=15.9 Hz), 12.71 (1H, s)<br>FAB−: 404, 406 |
| 211 | FAB−: 327 |

Example 212

To a solution of 180 mg of (2E)-3-[1-(phenylsulfonyl)-1H-indol-2-yl]acrylic acid in 3 mL of ethanol and 5 mL of methanol, 50 mg of 10% palladium-carbon (wet, water content 53%) was added, and the resulting mixture was stirred under hydrogen atmosphere (1 atm) at room temperature for 2 hours. The catalyst was removed from the solution, the solvent was evaporated under reduced pressure, and the residue was washed with ether to obtain 90 mg of 3-[1-(phenylsulfonyl)-1H-indol-2-yl]propanoic acid as a white solid. FAB−: 328

Example 213 a) Ethyl (2Z)-3-{1-[(4-bromophenyl)sulfonyl]-1H-indol-2-yl} acrylate

To a solution of 0.4 mL of ethyl di-o-tolylphosphonoacetate in 15 mL of THF was added 0.67 g of a 40% benzyltrimethylammonium hydroxide-methanol solution under cooling in a dry ice-acetone bath, and the resulting mixture was stirred at −70° C. for 15 minutes. To the solution, a solution of 0.47 g of 1-[(4-bromophenyl)sulfonyl]-1H-indole-2-carbaldehyde in 5 mL of THF was added, the resulting mixture was stirred at −70° C. for 1.5 hours and under cooling in an ice-methanol bath for 1 hour. To the solution, 50 mL of saturated aqueous sodium chloride solution was added, the mixture was extracted with 100 mL of ethyl acetate, the extract was washed with water and saturated aqueous sodium chloride solution and dried over anhydrous sodium sulfate, and the solvent was evaporated under reduced pressure. The residue was purified by silica gel column chromatography (ethyl acetate-hexane=1:5) to obtain 0.53 g of ethyl (2Z)-3-{1-[(4-bromophenyl)sulfonyl]-1H-indol-2-yl}acrylate as a pale yellow syrup. ESI−: 432, 434 b) (2Z)-3-{1-[(4-bromophenyl)sulfonyl]-1H-indol-2-yl} acrylic Acid

To a solution of 0.5 g of ethyl (2Z)-3-{1-[(4-bromophenyl)sulfonyl]-1H-indol-2-yl} acrylate in 4 mL of methanol and 0.4 mL of THF, 1.5 mL of a 1 M aqueous sodium hydroxide solution was added under ice cooling, and the resulting mixture was stirred under ice cooling for 2 hours and at room temperature for 3 hours. The solution was cooled with ice, 50 mL of water and 1.5 mL of 1 M hydrochloric acid were added, the mixture was extracted twice with 30 mL of chloroform, the extract was dried over anhydrous sodium sulfate, and then the solvent was evaporated under reduced pressure. The residue was purified by silica gel column chromatography (chloroform→chloroform-methanol=100:1→150:1) and then washed with hexane to obtain 0.28 g of (2Z)-3-{1-[(4-bromophenyl)sulfonyl]-1H-indol-2-yl}acrylic acid as a pale yellow solid. FAB−: 404, 406

Further, compounds listed in Tables 38 to 50 can be easily produced by the methods similar to those described in Examples above or applying the methods well known to the person skilled in the art based on these methods. These compounds are also included in the present invention.

TABLE 38

| No. | Ps | -A-(X)-(Ra¹)n |
|-----|-----|---------------|
| 1 | 3 | 6-methylnaphthalen-1-yl with NH-C6H4-Me(4) |
| 2 | 3 | 1-methylnaphthalene with 6-NO2 |
| 3 | 3 | 4-methyl-8-NO2 naphthalenyl |
| 4 | 3 | 4-methylnaphthalen-1-yl with NHC(O)-2,4-dichlorophenyl |
| 5 | 3 | 1-methyl-3,7-dichloronaphthalenyl |
| 6 | 3 | 4-methylnaphthalen-1-yl with CN |
| 7 | 3 | 5-methylnaphthalen-1-yl with CH2Ph |
| 8 | 3 | 4-methylnaphthalen-1-yl with NO2 |
| 9 | 3 | 4-methylnaphthalen-1-yl with COPh |
| 10 | 3 | 5-methylnaphthalen-1-yl with CN |
| 11 | 3 | 4-methylnaphthalen-1-yl with CH2CH3 |
| 12 | 3 | 5-methylnaphthalen-1-yl with OCH3 |

TABLE 39

[Structure: indole with COOH at position 4/5, N-sulfonyl-A-(X)(Ra¹)n]

| No. | Ps | —A—(X)(Ra¹)n |
|---|---|---|
| 13 | 3 | 5-methyl-1-naphthyl acetate (OC(O)CH₃) |
| 14 | 3 | 5-methyl-1-chloronaphthalene |
| 15 | 3 | 5-methyl-1-(trifluoromethyl)naphthalene |
| 16 | 3 | 5-methyl-2-(dimethylamino)naphthalene |
| 17 | 3 | 5-methyl-2-methoxynaphthalene |
| 18 | 3 | 6-methyl-2,3-dihydrobenzofuran |
| 19 | 3 | 5-methyl-8-fluoronaphthalene |
| 20 | 3 | 6-methyl-2,3-dihydro-1,4-benzodioxine |
| 21 | 3 | 5-methyl-1-(dimethylamino)naphthalene |
| 22 | 3 | 8-methylquinoline |
| 23 | 3 | 5-methyl-1-(acetylamino)naphthalene |
| 24 | 3 | 5-methyl-1-methyl-isatin (1-methyl-2,3-dioxoindoline) |

TABLE 40
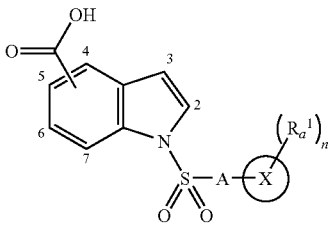
| No. | Ps | |
|---|---|---|
| 25 | 3 | 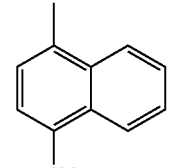 |
| 26 | 3 | 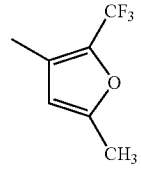 |
| 27 | 3 | 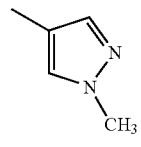 |
| 28 | 3 | 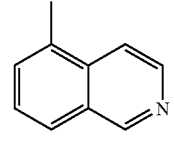 |
| 29 | 3 | 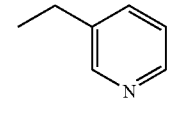 |
| 30 | 3 | 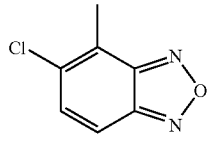 |
| 31 | 3 | 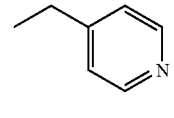 |
| 32 | 3 | 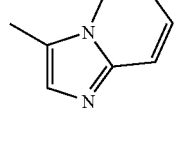 |
TABLE 40-continued
| No. | Ps | |
|---|---|---|
| 33 | 3 | 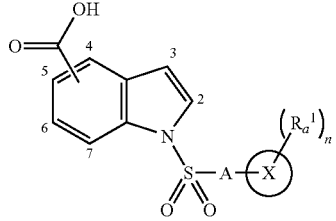 |
| 34 | 3 | 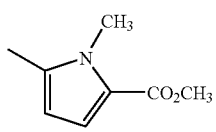 |
| 35 | 3 | 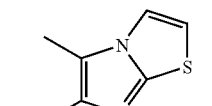 |
| 36 | 3 | 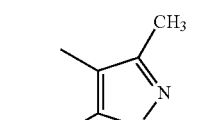 |
TABLE 41
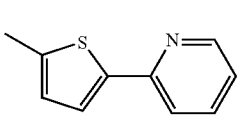
| No. | Ps | |
|---|---|---|
| 37 | 3 | 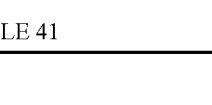 |
| 38 | 3 | 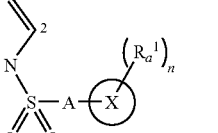 |

TABLE 41-continued
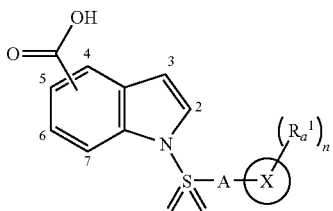
| No. | Ps | |
|---|---|---|
| 39 | 3 | 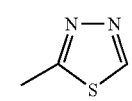 |
| 40 | 3 | 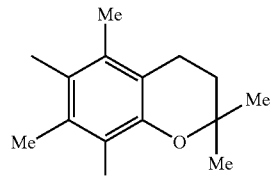 |
| 41 | 3 | 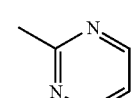 |
| 42 | 3 | 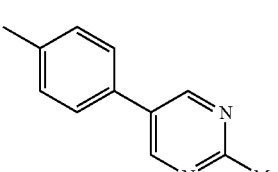 |
| 43 | 3 | 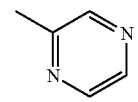 |
| 44 | 3 | 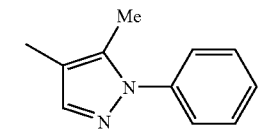 |
| 45 | 3 | 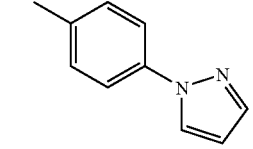 |
| 46 | 3 | 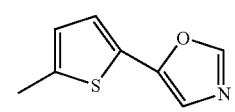 |
TABLE 41-continued
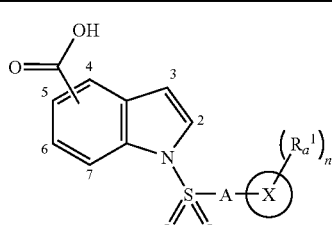
| No. | Ps | |
|---|---|---|
| 47 | 3 | 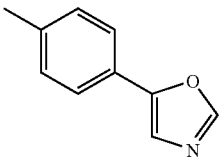 |
| 48 | 6 | 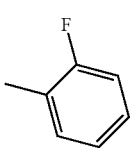 |
TABLE 42
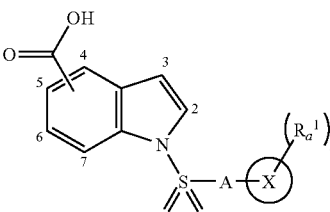
| No. | Ps | |
|---|---|---|
| 49 | 6 | 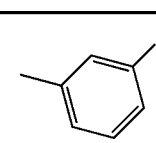 |
| 50 | 6 | 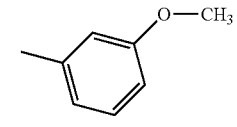 |
| 51 | 6 | 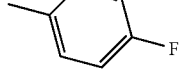 |

TABLE 42-continued
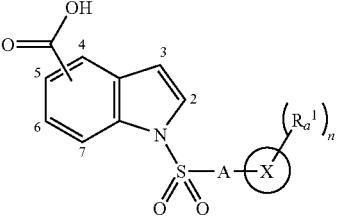
| No. | Ps | |
|---|---|---|
| 52 | 6 | 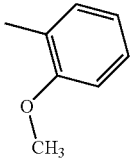 |
| 53 | 6 | 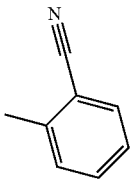 |
| 54 | 6 | 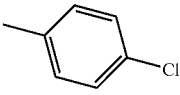 |
| 55 | 6 | 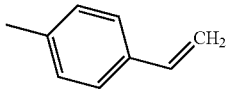 |
| 56 | 6 | 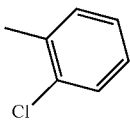 |
| 57 | 6 | 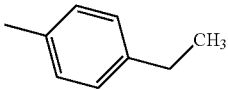 |
| 58 | 6 | 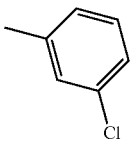 |
| 59 | 6 | 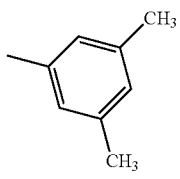 |
TABLE 42-continued
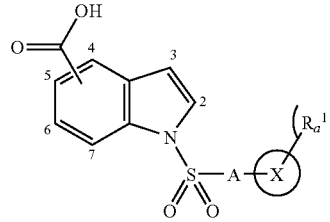
| No. | Ps | |
|---|---|---|
| 60 | 6 | 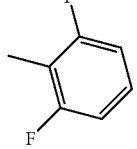 |
TABLE 43
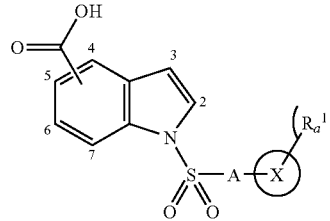
| No. | Ps | |
|---|---|---|
| 61 | 6 | 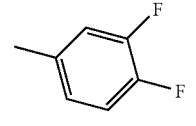 |
| 62 | 6 | 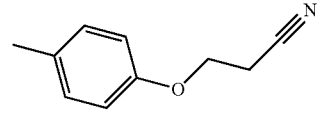 |
| 63 | 6 | 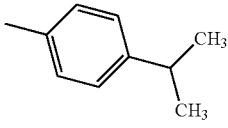 |
| 64 | 6 | 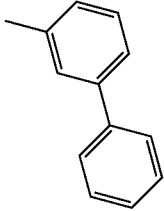 |

TABLE 43-continued
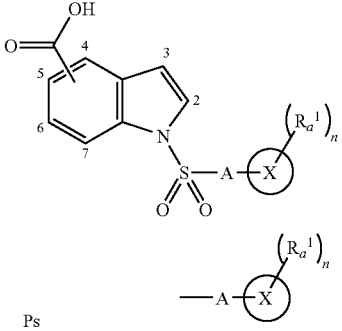
| No. | Ps | |
|---|---|---|
| 65 | 6 | 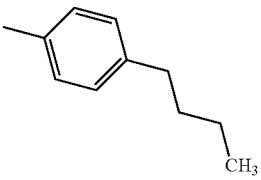 |
| 66 | 6 | 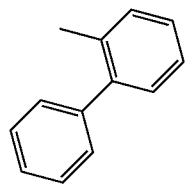 |
| 67 | 6 | 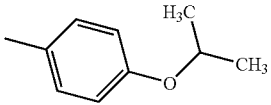 |
| 68 | 6 | 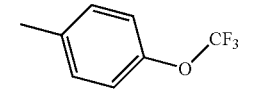 |
| 69 | 6 | 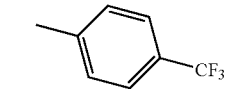 |
| 70 | 6 | 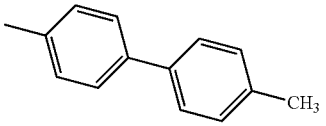 |
| 71 | 6 | 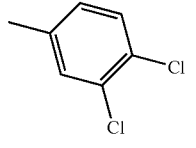 |
| 72 | 6 | 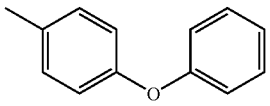 |
TABLE 44
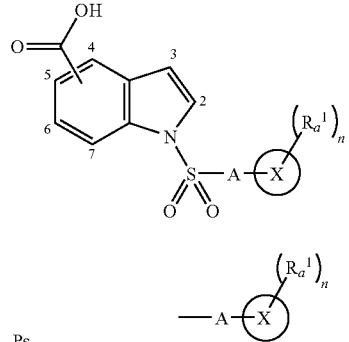
| No. | Ps | |
|---|---|---|
| 73 | 6 | 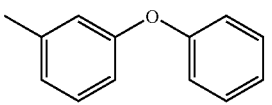 |
| 74 | 6 | 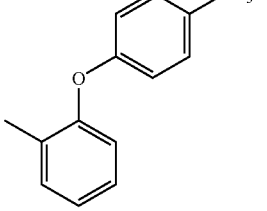 |
| 75 | 6 | 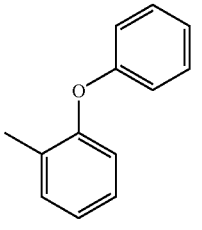 |
| 76 | 6 | 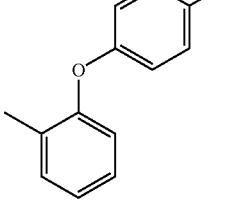 |
| 77 | 6 | 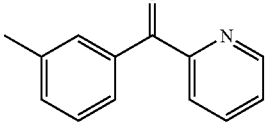 |
| 78 | 6 | 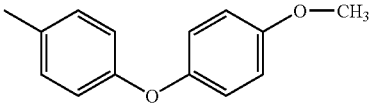 |
| 79 | 6 | 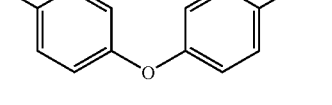 |

TABLE 44-continued
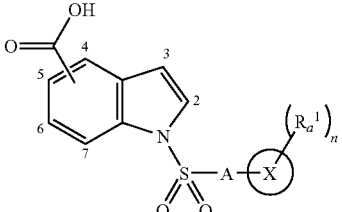
| No. | Ps | |
|---|---|---|
| 80 | 6 | 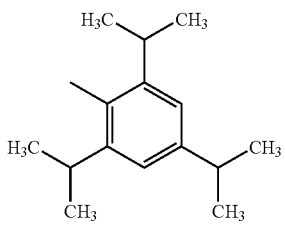 |
| 81 | 6 | 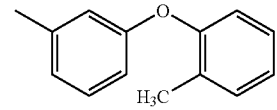 |
| 82 | 6 | 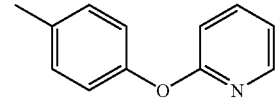 |
| 83 | 6 | 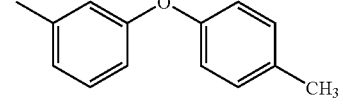 |
| 84 | 6 | 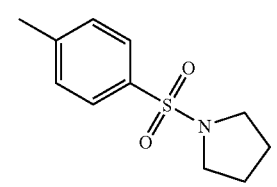 |
TABLE 45
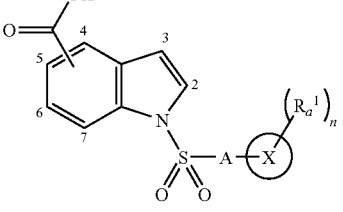
| No. | Ps | |
|---|---|---|
| 85 | 6 | 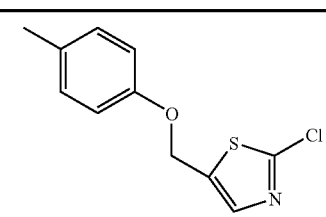 |
| 86 | 6 | 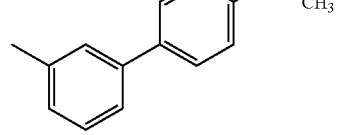 |
| 87 | 6 | 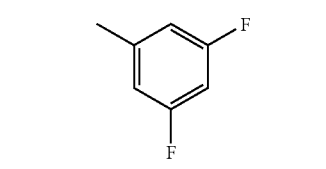 |
| 88 | 6 | 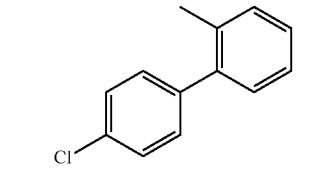 |
| 89 | 6 | 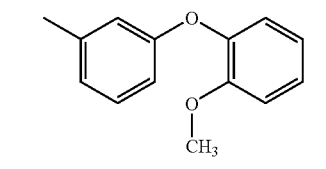 |
| 90 | 6 | 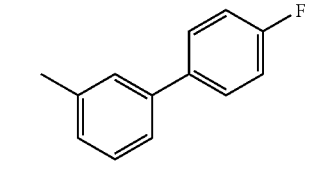 |
| 91 | 6 | 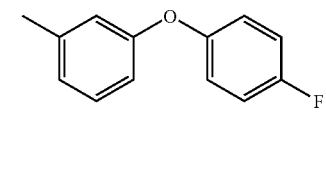 |

TABLE 45-continued
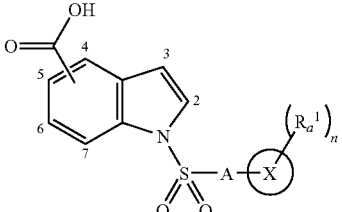
| No. | Ps | —A—(X)(Rₐ¹)ₙ |
|---|---|---|
| 92 | 6 | 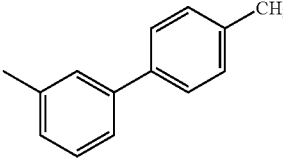 |
| 93 | 6 | 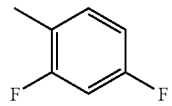 |
| 94 | 6 | 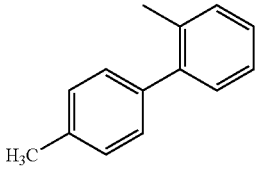 |
| 95 | 6 | 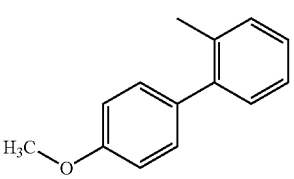 |
| 96 | 6 | 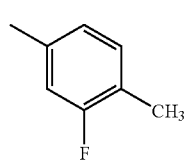 |
TABLE 46
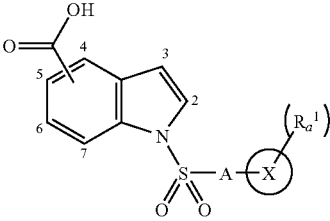
| No. | Ps | —A—(X)(Rₐ¹)ₙ |
|---|---|---|
| 97 | 6 | 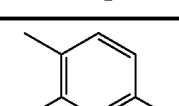 |
| 98 | 6 | 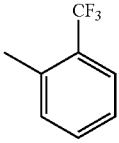 |
| 99 | 6 | 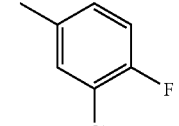 |
| 100 | 6 | 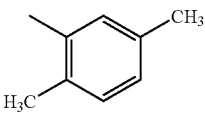 |
| 101 | 6 | 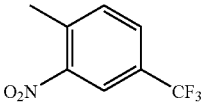 |
| 102 | 6 | 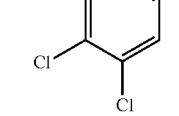 |
| 103 | 6 | 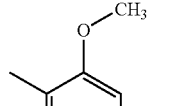 |
| 104 | 6 | 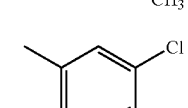 |
| 105 | 6 | 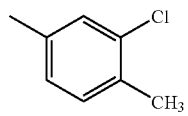 |

TABLE 46-continued

[Structure: indole-1-sulfonyl with 4-carboxylic acid, positions 2,3,5,6,7 labeled, N-SO2-A-(X)-(Ra1)n]

| No. | Ps | —A—(X)—(Ra¹)ₙ |
|---|---|---|
| 106 | 6 | 2,5-dimethyl-4-methoxyphenyl |
| 107 | 6 | 2-methyl-nitrobenzene (o-NO2, methyl) |
| 108 | 6 | 2-methyl-4-chloro-methoxyphenyl |

TABLE 47

[Structure: indole-1-sulfonyl with 4-carboxylic acid, positions 2,3,5,6,7 labeled, N-SO2-A-(X)-(Ra1)n]

| No. | Ps | —A—(X)—(Ra¹)ₙ |
|---|---|---|
| 109 | 6 | 2-methyl-6-chlorophenyl (CH3, Cl) |
| 110 | 6 | 2-methyl-4-chloro-fluorophenyl |
| 111 | 6 | 2-methyl-3-chlorophenyl |
| 112 | 6 | 2-methyl-3-chloro-fluorophenyl |
| 113 | 6 | 4-propyl-methylphenyl |
| 114 | 6 | 2-CF3-4-methyl-nitrophenyl |
| 115 | 6 | 2,5-difluoro-methylphenyl |
| 116 | 6 | 2,3-dimethyl-5-fluorophenyl |
| 117 | 6 | 3-CF3-methylphenyl |
| 118 | 6 | 2-methyl-4-ethyl-methoxyphenyl |

TABLE 47-continued
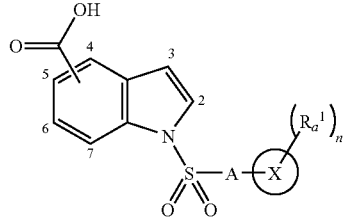
| No. | Ps | —A-(X)-(Ra¹)n |
|---|---|---|
| 119 | 6 | 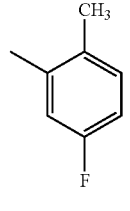 |
| 120 | 6 | 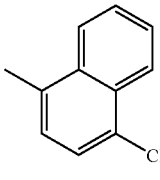 |
TABLE 48
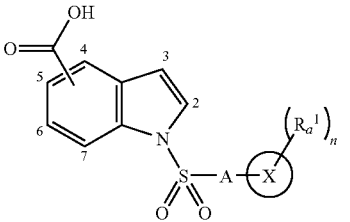
| No. | Ps | —A-(X)-(Ra¹)n |
|---|---|---|
| 121 | 6 | 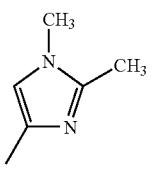 |
| 122 | 6 | 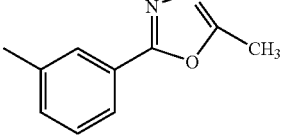 |
| 123 | 6 | 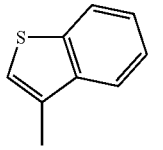 |
TABLE 48-continued
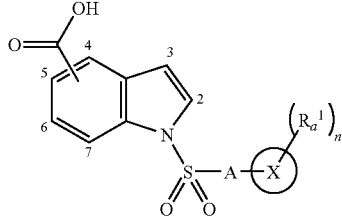
| No. | Ps | —A-(X)-(Ra¹)n |
|---|---|---|
| 124 | 6 | 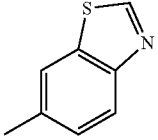 |
| 125 | 6 | 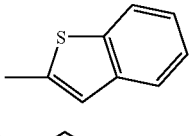 |
| 126 | 6 | 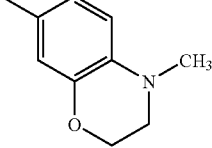 |
| 127 | 6 | 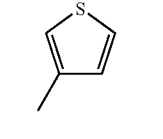 |
| 128 | 6 | 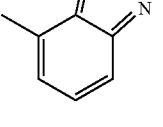 |
| 129 | 6 | 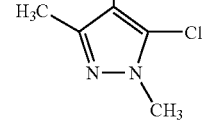 |
| 130 | 6 |  |
| 131 | 6 |  |

TABLE 48-continued
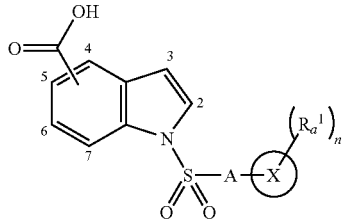
| No. | Ps | –A–X–(Ra¹)n |
|-----|----|----|
| 132 | 6 |  |
TABLE 49
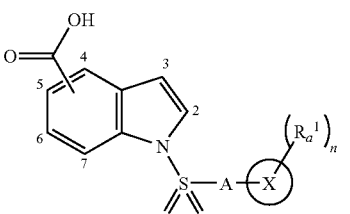
| No. | Ps | –A–X–(Ra¹)n |
|-----|----|----|
| 133 | 6 | 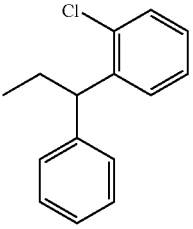 |
| 134 | 6 | 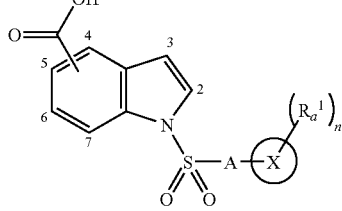 |
| 135 | 6 | 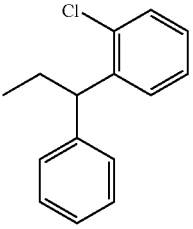 |
| 136 | 6 | 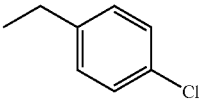 |
| 137 | 6 | 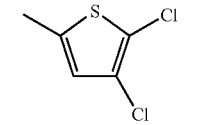 |
TABLE 49-continued
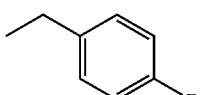
| No. | Ps | –A–X–(Ra¹)n |
|-----|----|----|
| 138 | 6 | 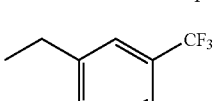 |
| 139 | 6 | 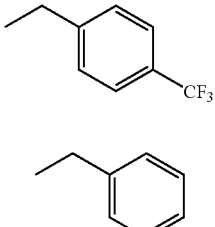 |
| 140 | 6 | 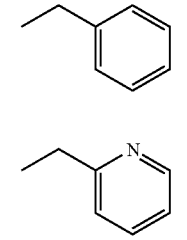 |
| 141 | 6 | 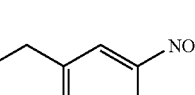 |
| 142 | 6 | 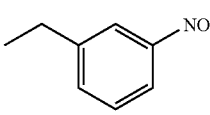 |
| 143 | 6 | 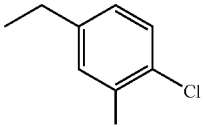 |
| 144 | 6 | 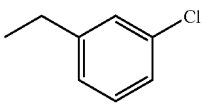 |

TABLE 50

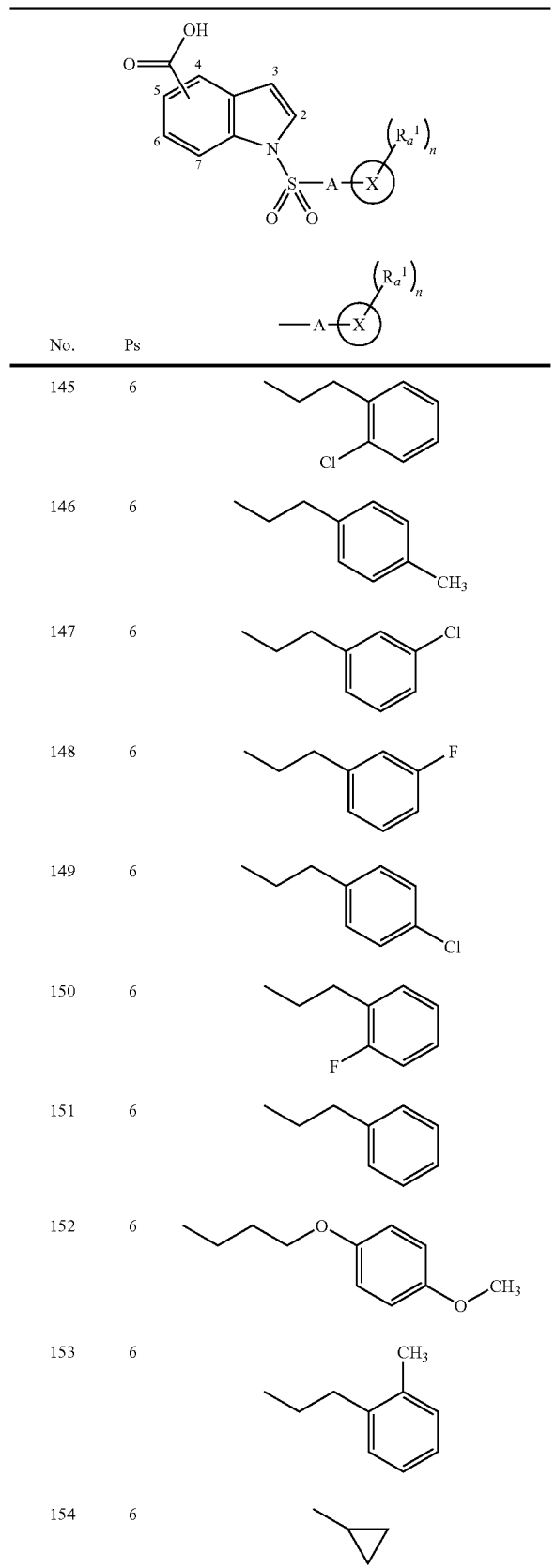

| No. | Ps | —A—(X)(Ra¹)n |
|-----|----|----|
| 145 | 6 | |
| 146 | 6 | |
| 147 | 6 | |
| 148 | 6 | |
| 149 | 6 | |
| 150 | 6 | |
| 151 | 6 | |
| 152 | 6 | |
| 153 | 6 | |
| 154 | 6 | |

TABLE 50-continued

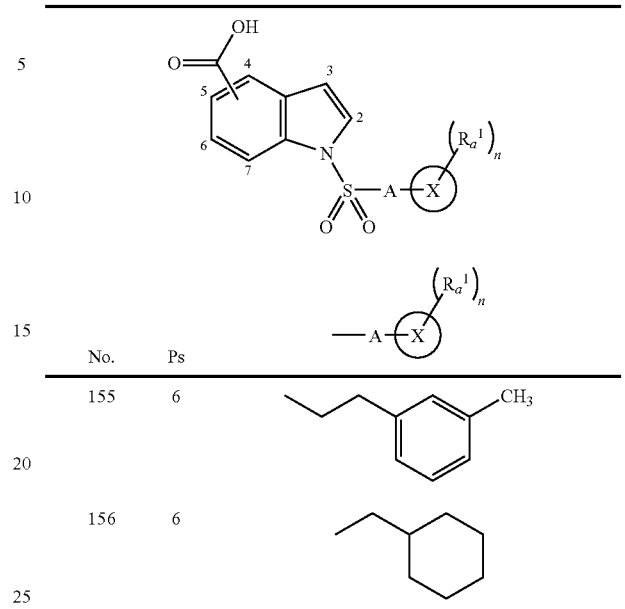

| No. | Ps | —A—(X)(Ra¹)n |
|-----|----|----|
| 155 | 6 | |
| 156 | 6 | |

(Pharmacological Test)

An excellent selective inhibitory activity against human 17βHSD type 5 of the compounds of the present invention was confirmed by a test method described below. Further, the test may be performed by referring to the details of test procedure described in Maniatis, T. et al., Molecular Cloning—A Laboratory Manual Cold Spring Harbor Laboratory, NY and the like (1982). In addition, a gene encoding human 17βHSD type5 and type3 described in 1 and 2 below, and human 17βHSD type5 and type3 may be obtained by the method described in Mol. Endocrinol, 1971-1984, 11(13) (1997).

1. Isolation of Gene Encoding Human 17βHSD Type 5 and Purification of Enzyme

A full-length cDNA encoding human 17βHSD type 5 used in the pharmacological test of the present invention was obtained by the PCR method using a cDNA derived from a human lung cancer-derived cell line, A549 cells as a template. The nucleotide sequence of the obtained cDNA was analyzed by the dideoxyterminator method, and the clone matched with the known human 17βHSD type 5 sequence (GenBank accession No. NM_003739) was selected. Escherichia coli BL21 was transformed with a plasmid containing the cDNA, cultured on a large scale, and the proteins were purified by using GSTrapFF column (Amersham) and PreScissionProtease (Amersham). The purification was performed in accordance with the instructions attached to the GSTrapFF column.

2. Isolation of Gene Encoding Human 17βHSD Type 3 and Purification of Enzyme

A full-length cDNA encoding human 17βHSD type 3 used in the pharmacological test of the present invention was obtained by the PCR method using a cDNA derived from human testis as a template. The nucleotide sequence of the obtained cDNA was analyzed by the dideoxyterminator method, and the clone matched with the known human 17βHSD type 3 sequence (GenBank accession No. BC034281) was selected. Subsequently, a human fetus kidney-derived cell line, 293 cells was transformed with a plasmid containing the cDNA, and the cells were collected 24 hours later. The collected cells were then disrupted in a phosphate buffer solution containing 5% glycerol (500 μL per 100 mm-dish of a phosphate buffer solution (pH 7.4, 200 mM) containing 5% glycerol) and centrifuged (16000 rpm, 5 min, 4° C.), and the supernatant was used as an enzyme source.

3. Measurement of Enzyme Activities of Human 17βHSD Type 5 and Type 3

Enzyme activity was measured referring to Trevor M. Penning, et al., Biochem. J., 351, 67-77, (2000). Specifically, using a 100 mM potassium phosphate buffer (pH 6.0), (1) the enzyme purified in above 1 at a final concentration of 10 μg/mL, (2) andiostenedione at a final concentration of 300 nM, (3) NADPH at a final concentration of 200 μM and (4) a test substance at a final concentration of 3 μM were mixed to react at room temperature for 2 hours, and then the amount of testosterone produced was measured using DELFIA (registered trademark) Testosterone Reagents R050-201 (PerkinElmer). The measurement was performed in accordance with the attached instructions. The amount of reduction of testosterone production in the presence of the compound was obtained as a relative value with respect to the amount of testosterone in the absence of the enzyme set at 0% and the amount of testosterone produced in the absence of the compound set at 100%. Then, $IC_{50}$ values were calculated by the Logistic regression method.

The $IC_{50}$ values of inhibitory activity against human 17βHSD type 5 and type 3 of the Example compounds included in the compounds of the present invention are shown in Table 51. In addition, the $IC_{50}$ values of inhibitory activity against human 17βHSD type 5 of the compounds described in Non-patent Document 19 and confirmed to be effective for Ehrlich ascites tumor are shown in Comparative Examples (1) and (2) in Table 51. The structural formula of the compounds in Comparative Examples (1) and (2) are shown below.

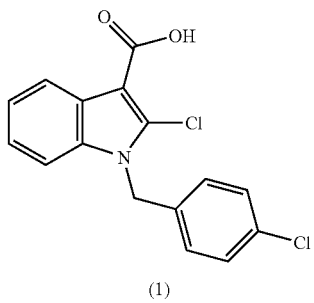

[formula 33]

(1)

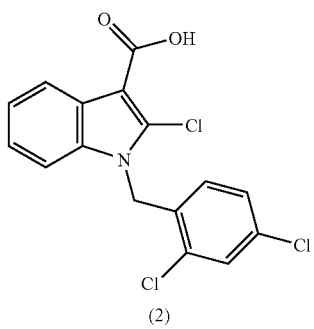

(2)

| Ex | $IC_{50}$ (μM) | |
|---|---|---|
| (CEx) | Type 5 | Type 3 |
| 144 | 0.090 | >10 |
| 190 | 0.69 | >10 |

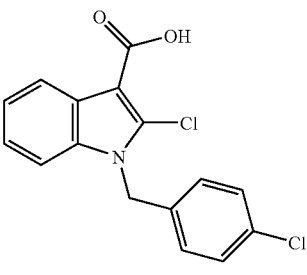

-continued

[formula 33]

(1)

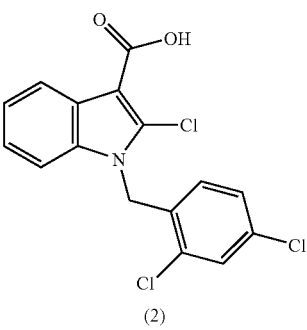

(2)

| Ex | $IC_{50}$ (μM) | |
|---|---|---|
| (CEx) | Type 5 | Type 3 |
| 155 | 5.5 | >10 |
| 191 | 0.30 | >10 |
| 175 | 0.12 | 8.9 |
| 163 | 0.22 | >10 |
| 192 | 0.069 | >10 |
| 187 | 2.2 | >10 |
| 168 | 0.085 | >10 |
| 193 | 0.13 | >10 |
| 194 | 0.19 | 6.2 |
| 203 | 2.0 | >10 |
| 208 | 2.2 | >10 |
| 138 | 0.33 | >10 |
| 133 | 3.1 | >10 |
| (1) | >10 | — |
| (2) | >10 | — |

CEx: Comparative Example

As shown by the test results above, the compounds of the present invention represented by formula (I) and/or formula (II) and/or formula (III) scarcely have inhibitory activity against human 17βHSD type 3 and have inhibitory activity selective to human 17βHSD type 5. In addition, the compounds of Comparative Examples (1) and (2) that are known to be effective for Ehrlich ascites tumor scarcely exhibited 17βHSD type 5 inhibitory activity.

4. Measurement of Concentrations of Human 17βHSD Type 5 Inhibitor Compounds in Mouse Tissues The concentrations in plasma and in prostate were measured after oral administration of a test substance. Male 8 to 15-week old ICR mice were used, and a solution or suspension obtained by adding 1 N NaOH solution and water in an equivalent amount to a test substance and stirring was used as an administration solution. The administration solution was administered orally once to mice, and after 2 hours, blood and a prostate were collected under ether anesthesia. The prostate was frozen and stored at −80° C. until measurement. The blood was centrifuged (3000 rpm, 15 min, 4° C.) after the addition of a minor amount of heparin, and the upper layer was collected as plasma and frozen and stored at −80° C. until measurement. 0.1 mL of the plasma was subjected to protein degeneration with 0.1 mL of acetonitrile and then centrifuged (15000 rpm, 7 min, 4° C.) to remove proteins and the supernatant thus obtained was used as an HPLC sample. The prostate was homogenized in a phosphate buffer solution (200 mM, pH 7.4, 0.5 mL), and then the whole volume was added to 3 mL of t-butyl methyl ether to perform extraction. The solvent was evaporated in a stream of nitrogen (15 min, 45° C.). The residue was resuspended in a Tris buffer solution (12.5 mM, pH 7.4, 0.3 mL) containing 2% BSA, and an equal volume of acetonitrile (0.3 mL) was added. Protein was removed as in the case of plasma and the supernatant was used as an HPLC measurement sample. Measurement was performed by an ordinary method using liquid chromatography (HPLC). The results are described in Table 52.

<HPLC Conditions>
Column: STR ODS-II (registered trademark), particle size: 5 μm, inner diameter: 4.6 mm, length: 150 mm, joint type: Waters
Mobile phase: 20 mM ammonium acetate:acetonitrile=7:3 or 17 mM ammonium acetate:acetonitrile=6:4
Flow rate: 1 mL/min
Column temperature: 40° C.
Injection volume: 50 μL

TABLE 52

| Ex | Dose (mg/kg) | Conc (plasma) (uM) | Conc (prostate) (uM) |
|---|---|---|---|
| 1 | 30 | 17.0 | 5.3 |
|   | 100 | 57.4 | 13.3 |
|   | 300 | 145.1 | 47.4 |
| 144 | 100 | 38.5 | 7.2 |
|   | 300 | 79.1 | 24.8 |
| 190 | 300 | 225.5 | 37.4 |
| 155 | 100 | 88.4 | 23.0 |
| 175 | 100 | 83.8 | 8.6 |
| 163 | 100 | 88.8 | 19.1 |
| 192 | 100 | 57.3 | 9.4 |
|   | 300 | 126.1 | 24.9 |
| 187 | 100 | 69.7 | 12.2 |

Dose: dose,
Conc (plasma): concentration in the plasma,
Conc (prostate): concentration in prostate As shown by the test results above, the compounds of formula (I) and/or (II) and/or formula (III) show good oral drug absorption and prostate distribution. Since the compounds of formula (I) and/or (II) and/or formula (III) have very weak inhibitory activity against human 17βHSD type 3, it is expected to suppress intracrine testosterone synthesis selectively in the prostate by their selective inhibitory effect against 17βHSD type 5 without affecting biosynthesis of testosterone derived from human 17βHSD type in the testes, thus useful especially for treating and/or preventing benign prostatic hyperplasia and prostatic cancer without adverse drug reactions.

A pharmaceutical composition containing the compound of formula (I) and/or formula (II) and/or formula (III) or a pharmaceutically acceptable salt thereof as an active ingredient can be prepared using a carrier, an excipient, and other additives that are generally used for formulation.

Administration may be any of oral administration using tablets, pills, capsules, granules, powders, liquids and the like, or parenteral administration using injections such as intravenous injection, intramuscular injection and the like, suppositories, percutaneous preparations, nasal preparations, inhalation preparations or others. The dose is determined accordingly taking symptoms, age and sex of a subject and the like into consideration depending on each case. The dose is generally around 0.001 to 100 mg/kg/day for an adult in the case of oral administration, and the daily dose is administered in a single dose or 2 to 4 divided doses. When it is administered intravenously according to symptoms, it is administered one to several times a day at a dose in the range of 0.0001 to 10 mg/kg/dose for an adult. In the case of inhalation, it is administered one to several times a day at a dose in the range of 0.0001 to 1 mg/kg/dose for an adult.

As a solid composition for oral administration according to the present invention, tablets, powder, granules and the like are used. In such solid composition, one or more active ingredients are mixed with at least one inactive excipient, for example, lactose, mannitol, glucose, hydroxypropylcellulose, microcrystalline cellulose, starch, polyvinyl pyrrolidone, magnesium aluminometasilicate and the like. The composition may contain, according to an ordinary method, inactive additives, for example, lubricants such as magnesium stearate and the like, disintegrants such as sodium carboxymethyl starch and the like, and solubilization assisting agents. Tablets or pills may be sugar-coated or coated with a gastric dissolving or enteric coating, if necessary.

A liquid composition for oral administration includes pharmaceutically acceptable emulsion, solution, suspension, syrup, elixir and the like, and contains inert solvents used in general, for example, purified water and ethanol. The composition may contain, in addition to the inert solvent, auxiliary agents such as solubilizing agents, moistening agents, and suspending agents; sweeteners; flavoring agents; fragrances; and preservatives.

An injection for parenteral administration includes sterile aqueous or non-aqueous solution, suspension, and emulsion. Examples of aqueous solvents include, for example, distilled water for injection and physiological saline solution. Examples of non-aqueous solvents include, for example, propylene glycol, polyethylene glycol, vegetable oils such as olive oil, alcohols such as ethanol, polysorbate 80 (Pharmacopoeia name) and the like. The composition may further contain tonicity agents, preservatives, moistening agents, emulsifiers, dispersing agents, stabilizers, and solubilizing agents. The composition is sterilized by, for example, filtration through a bacteria-retaining filter, incorporation of a bactericide or irradiation. In addition, a sterile solid composition may be first produced, and then dissolved or suspended in sterile water or sterile solvent for injection before use, and then used.

Transmucosal preparations such as inhalation preparations, transnasal preparations and the like are used in a solid, liquid, or semisolid form, and can be produced by the method conventionally known. For example, excipients such as lactose and starch, and further, pH adjusting agents, preservatives, surfactants, lubricants, stabilizers, and thickeners and the like may be appropriately added. For administration, an appropriate device for inhalation or insufflation may be used. For example, using known devices such as a metered dose inhalation device or spray device, the compound can be administered alone or as powder of a formulated mixture or a solution or suspension in combination with pharmaceutically acceptable carriers. A dry powder inhaler and the like may be for single dose or multiple dose, and dry powder or powder-containing capsule may be used. Alternatively, a pressurized aerosol spray and the like using an appropriate gas, such as propellants, for example, chlorofluoroalkane, hydrofluoroalkane, carbon dioxide or the like.

In producing suppositories, a low melting point wax, for example, a fatty acid glyceride mixture or cocoa butter is melted, and an active ingredient is added and dispersed homogeneously by stirring. After that, the mixture is injected into an appropriate mold and cooled for solidification. Liquid preparations include solution, suspension, retention enema and emulsion, for example, a water or aqueous propylene glycol solution.

INDUSTRIAL APPLICABILITY

Since the compound, an active ingredient of the medicament of the present invention, has a selective inhibitory effect against 17βHSD type 5 and a superior pharmacological effect based thereon, the pharmaceutical composition according to the present invention is useful as a therapeutic and/or preventive agent for diseases associated with 17βHSD type 5, particularly prostatic cancer, benign prostatic hyperplasia, acne, seborrhea, hirsutism, baldness, alopecia, precocious puberty, adrenal hypertrophy, polycystic ovary syndrome, breast cancer, lung cancer, endometriosis, leiomyoma or the like.

The invention claimed is:

1. A compound or a pharmaceutically acceptable salt thereof, which is selected from 1-[(4-bromophenyl)sulfonyl]-1H-indole-3-carboxylic acid, 4-methoxy-1-(phenylsulfonyl)-1H-indole-3-carboxylic acid, 5-methyl-1-(phenylsulfonyl)-1H-indole-3-carboxylic acid, 5-fluoro-1-(phenylsulfonyl)-1H-indole-3-carboxylic acid, 7-fluoro-1-(phenylsulfonyl)-1H-indole-3-carboxylic acid, 1-[(4-bromophenyl)sulfonyl]-7-chloro-1H-indole-3-carboxylic acid, 7-chloro-1-(phenylsulfonyl)-1 H-indole-3-carboxylic acid, and 5-chloro-1-(phenylsulfonyl)-1 H-indole-3-carboxylic acid.

* * * * *